United States Patent [19]
Gilham

[11] Patent Number: 5,291,400
[45] Date of Patent: Mar. 1, 1994

[54] SYSTEM FOR HEART RATE VARIABILITY ANALYSIS

[75] Inventor: Jeffrey J. Gilham, Seattle, Wash.

[73] Assignee: SpaceLabs Medical, Inc., Redmond, Wash.

[21] Appl. No.: 866,806

[22] Filed: Apr. 9, 1992

[51] Int. Cl.$^5$ .................. G06F 15/42; A61B 5/04
[52] U.S. Cl. ................... 364/413.06; 128/702
[58] Field of Search ............ 364/413.05, 413.06; 128/702, 703, 704, 705

[56] References Cited

U.S. PATENT DOCUMENTS 5,046,504 9/1991 Albert et al. ............... 364/413.06
5,109,862 5/1992 Kelen et al. ................ 364/413.06

Primary Examiner—Donald E. McElheny, Jr.
Attorney, Agent, or Firm—Seed and Berry

[57] ABSTRACT

A method and system for heart variability analysis is provided. A computer system generates various statistical and spectral measurements of heart rate variability based on user-specified qualifications and displays the results. The computer system includes a statistical and spectral data component. The spectral component includes a data storage device for storing electrocardiographic data, an interval detector for determining the length of heart beat intervals in the electrocardiographic data, an instantaneous interval function data generator for generating instantaneous interval function data based on the interval data and user-specified qualifications, a filter and resampler for generating resampled data by filtering and resampling the instantaneous interval function data, a power spectral density data generator for generating spectral density data based on the resampled data and user-specified qualifications, a period spectral data generator for accumulating period and region spectral data measurements based on the generated power spectral density data, a time period, and user-specified qualifications, and a display controller for displaying period data and region data. The invention allows a user to specify minimum and maximum beat interval times, whether intervals near atrial and ventricular ectopic beats should be disregarded, the time period over which data is to be accumulated, the difference margins for beat triplets, the region of time over which data is accumulated, and whether data is to be displayed in graphical or tabular format.

33 Claims, 30 Drawing Sheets

HR Variability
Mode  Resolution

HRV Statistical Configuration

Interval Qualification — 301

Minimum Interval Threshold (msec): 300
Maximum Interval Threshold (msec): 1500
Intervals To Exclude Before SVEs: 1
Intervals To Exclude After SVEs: 1
Intervals To Exclude Before VEs: 1
Intervals To Exclude After VEs: 1

Period Qualification — 302

Minimum Qualified Intervals Per Min: 10
Minimum Qualified Triplets Per Min: 10

Difference Qualification — 303

RR Difference Margin (msec): 50

GENERATE   CANCEL

SYSTEM FOR HEART RATE VARIABILITY ANALYSIS

TECHNICAL FIELD

This invention relates generally to a system for analyzing electrocardiographic data, and more specifically, to a method and system for analyzing and displaying heart rate variability data.

BACKGROUND OF THE INVENTION

Electrocardiograms are commonly used to generate data relating to the health and operation of a patient's heart. ECG data is useful to study heart rate variability, that is, variations in a patient's pulse over time. The study of heart rate variability (HRV) is useful as a noninvasive indicator of parasympathetic and sympathetic influences on the heart. HRV analysis has been used to study sudden infant death syndrome, autonomic neuropathy, brain stem status, brain death, the staging of diabetic neuropathy, hypertension, acute myocardial infarction, congestive heart failure, and sudden cardiac death.

The appeal of HRV analysis has increased with the development of Holter recorders. A Holter recorder is used to collect ECG data over a period of several days in ambulatory patients. Thus, ECG data can be collected in a setting that represents a patient's typical day. Holter recorders record large amounts of data that may be difficult for a clinician to analyze.

Several computer systems have been developed to perform statistical and spectral HRV analysis. These prior art systems, however, are not particularly useful to a clinician because of their lack of flexibility. The developers of these prior art systems have established certain methods for analyzing and displaying the HRV data. These methods, however, do not correspond to a preferred method of analyzing and displaying in many situations. For example, these prior art systems may not allow for the display of summary information over certain time periods (e.g., sleeping). Also, these systems do not permit the tailoring of the analysis to address a specific patient's heart rate condition.

It would be desirable to have an HRV system that would allow the clinician considerable freedom to control the statistical and spectral analysis in on-screen and printed format of reported data.

SUMMARY OF THE INVENTION

It is an object of the present invention to provide a method and system for heart rate variability analysis.

It is another object of the present invention to provide a method and system which allows a clinician to define beat interval qualifications, which include a minimum and maximum beat interval time and proximity of an interval to an atrial or a ventricular ectopic beat.

It is another object of the present invention to provide a method and system in which a clinician can specify the minimum number of intervals or triplets that must occur every minute to ensure the validity of the data.

It is another object of the present invention to provide a method and system in which a clinician can specify a maximum difference in interval times between intervals in a triplet to ensure the validity of the data.

It is another object of the present invention to provide a method and system for reviewing statistical HRV data on screen in both tabular and graphical format.

It is another object of the present invention to provide a method and system which allows a clinician to specify time periods of resolution for the accumulation of HRV data.

It is another object of the present invention to provide a method and system which allows a clinician to specify a region of ECG data, which may comprise noncontiguous time ranges, for which a slimmary statistical data is generated.

It is another object of the present invention to provide a method and system for updating summary data on the screen as the clinician redefines the region.

It is another object of the present invention to provide a method and system for printing tabular or graphical reports based on the clinician-defined resolution and region.

It is another object of the present invention to provide a method and system for allowing the user to specify power spectral density time bases for a spectral analysis. A time base specifies the lowest resolution of spectral analysis.

It is another object of the present invention to allow a method and system in which a clinician may define low-frequency, mid-frequency, and high-frequency bands and for which summary data is accumulated.

It is another object of the present invention to provide a method and system in which a clinician may review power spectral data on the screen in a clinician-specified resolution.

It is another object of the present invention to provide a method and system in which data included within the region and excluded from the region can be differentiated on the screen.

It is another object of the present invention to provide a method and system for displaying the low-frequency, mid-frequency, high-frequency, and total frequency power, and the total low-frequency power to total high-frequency power ratio, as well as the amount of included and excluded data and the percentage of included data which meets the clinician-specified qualifications.

It is another object of the present invention to provide a method and system in which power spectral graphs can be automatically displayed in rapid succession.

It is another object of the present invention to provide printed reports corresponding to the data displayed on the screen.

These and other objects of the invention, which will be apparent as the invention is more fully described below, are obtained by providing, in a preferred embodiment, a computerized system for HRV review and analysis of statistical and spectral data. In a preferred embodiment, the HRV system includes a statistical and spectral component. In a preferred embodiment, the statistical component of the HRV system includes a storage device for storing electrocardiographic data, an interval detector for determining the length of heart beat intervals in the electrocardiographic data, a minute data generator for accumulating statistical measurements based on the intervals and user-specified qualifications, a period data generator for accumulating statistical data measurements based on the generated minute data, period time, and user-specified qualifications, a region data generator for accumulating statistical measurements based on the generated minute data for a region of time, and a display controller for displaying the period data and region data. In a preferred embodiment, a user specifies a minimum and maximum interval time that the system uses when detecting intervals. The system also excludes intervals that are within a user-defined proximity of an atrial or ventricular ectopic beat. The system disregards a minute of data when the user-specified minimum number of intervals or triplets is not within the minute. The system also displays period data in tabular or graphical format on a computer display device. The system accumulates period data based on the user-specified time periods and accumulates region data based on user-specified time ranges. The system updates region data automatically as the user defines a region. In a preferred embodiment, the spectral component of the HRV system includes a storage device for storing electrocardiographic data, an interval detector for determining the length of heart beat intervals in the electrocardiographic data, an instantaneous interval function generator for generating an instantaneous interval function data based on the interval data and user-specified qualifications, a filter and resampler for generating resampled data by filtering and resampling the instantaneous interval function, a power spectral density generator for generating spectral density data based on the resampled data and user-specified qualifications, a period spectral data generator for accumulating period spectral data measurements based on the generated power spectral density, a time period, and user-specified qualifications, and a display controller for displaying period data and region data.

BRIEF DESCRIPTION OF THE DRAWINGS

FIG. 3 shows a sample display for input of the user-specified qualifications for statistical analysis.

FIG. 6 shows a sample display for input of user-specified interval qualifications and the time base for spectral analysis.

DETAILED DESCRIPTION OF THE INVENTION

The present invention provides a heart rate variability analysis system that allows a user (clinician) to review statistical and spectral HRV data. The HRV system can display and print statistical data in both tabular and graphical format. The HRV system inputs beat data (location in time, diagnosis, and clinical interpretation) for every beat derived from beat data for a scan period, which may encompass many hours of data. Beat data is also ref erred to as an annotated beat list. The HRV system inputs various user-specified parameters, analyzes beat data to calculate inter-beat time intervals, and generates various statistical and spectral graphs and reports relating to the heart rate variability. The HRV system comprises a statistical portion and a spectral portion for generating statistical and spectral data, respectively.

Figure 8:
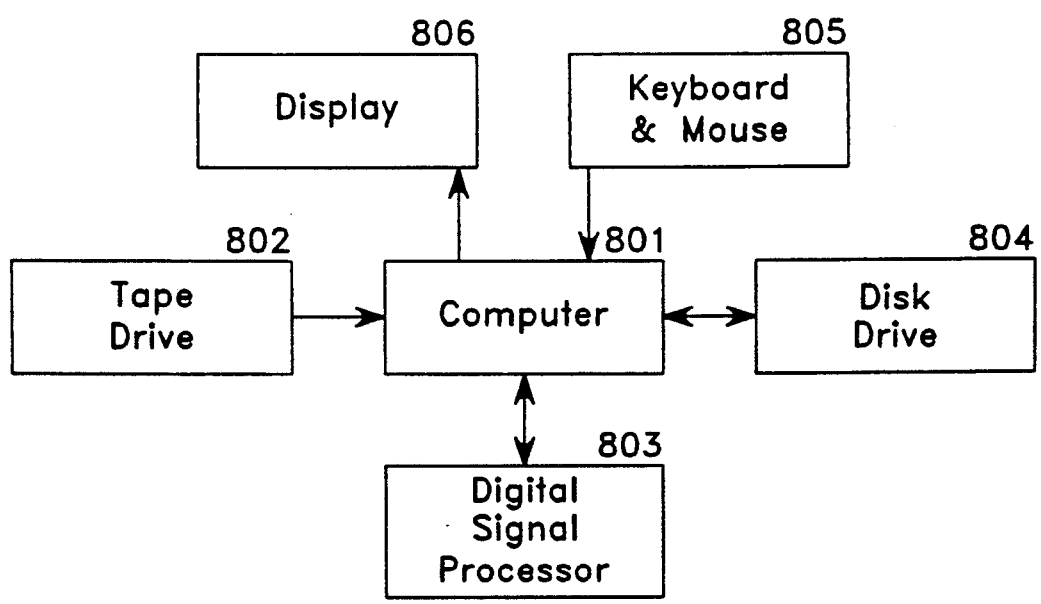
FIG. 8 is an overview schematic diagram of a computer system implementing a preferred embodiment of the present invention.

FIG. 8 is a block diagram of a computer system implementing a preferred embodiment of the present invention. The computer system comprises computer 801, tape drive 802, digital signal processor 803, disk drive 804, keyboard and mouse 805, and display 806. Computer 801 is any one of a variety of general-purpose computers, such as those based on the Intel 80386 or 80486 processor. Computer 801 receives analog ECG data from tape drive 802. The ECG data may be collected by a Holter recorder or any of a variety of ECG recording devices. Computer 801 uses digital signal processor 803 to digitize the ECG data. Computer 801 stores the digitized ECG data either in memory or on disk drive 804. Computer 801 processes ECG data based on user input received through the keyboard and mouse 805, displays statistical and spectral data on display 806, and prints statistical and spectral data on a printer.

STATISTICAL DATA INTERFACE

The HRV system generates six statistical measurements of heart rate variability for each user-specified time period within the scan period of beat data. The six time period statistical measurements are:

1. the number of qualified intervals (two successive beats);
2. the mean interval time;
3. the standard deviation of the interval times;
4. the number of qualified triplets;
5. the root mean square of successive differences of interval times within a triplet (RMSSD); and
6. the percent of triplets whose difference in interval times exceeds a user-specified amount (%RRxx).

Figure 1:
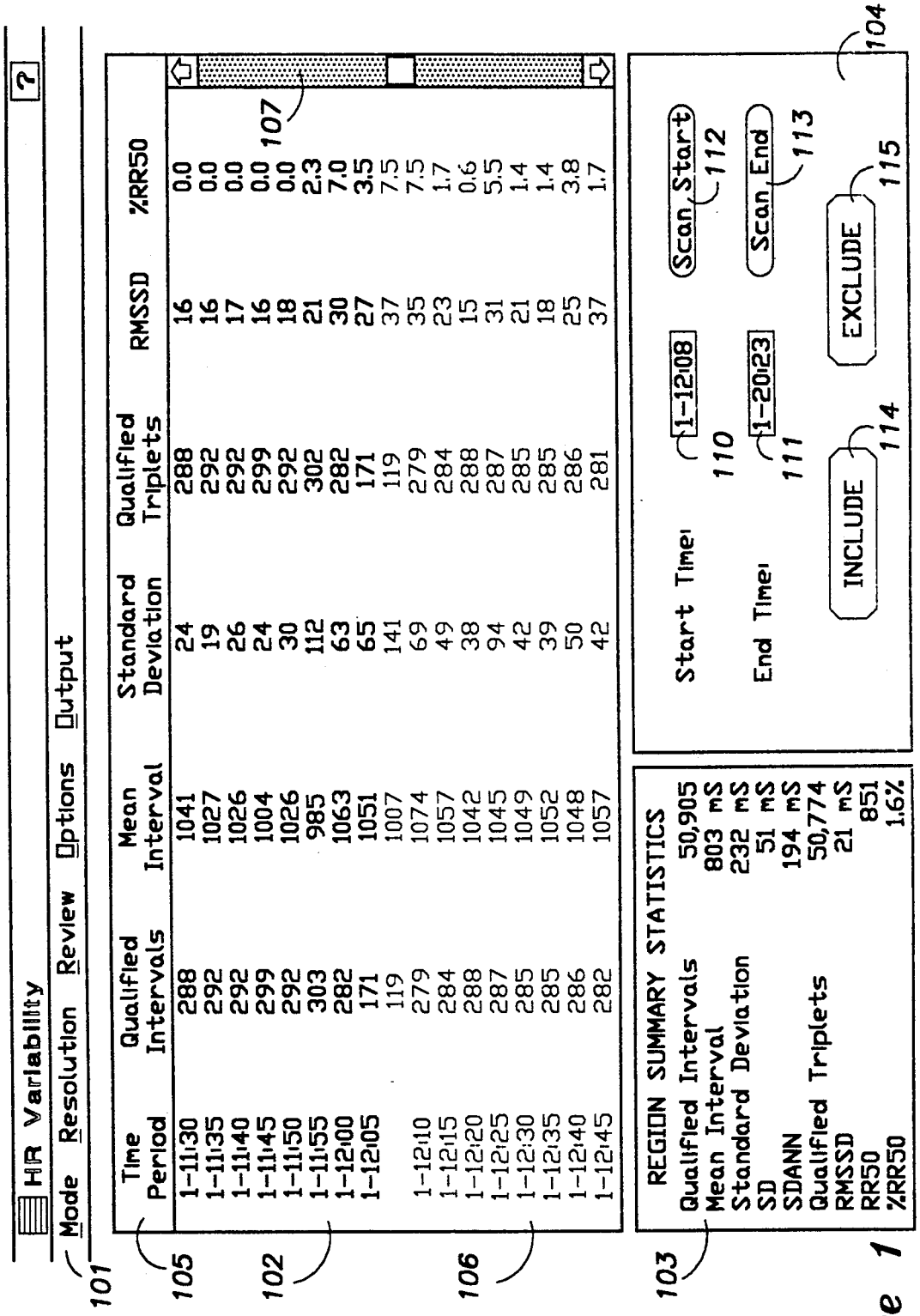
FIG. 1 shows a sample display of HRV statistical data in tabular format.
Figure 2:
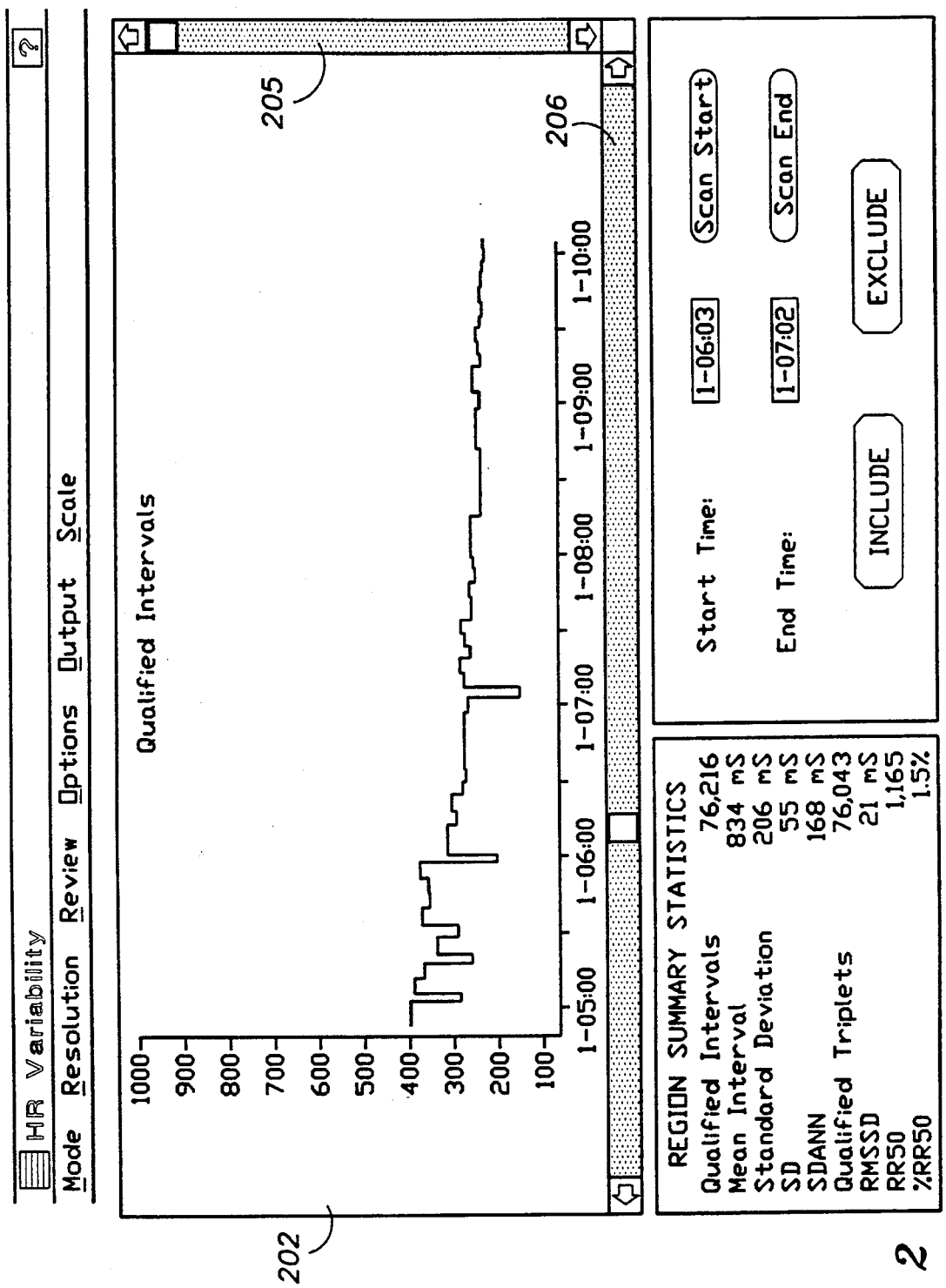
FIG. 2 shows a sample display of HRV statistical data in graphical format.

The calculation of these six measurements is described below in detail. The HRV system allows the user to specify the length of the time period for which these six statistical measurements are accumulated. For example, the user may select a time period (or resolution) of 1, 5, 15, or 60 minutes. If the user selects a time period of 5 minutes, then the HRV system accumulates these six statistical measurements for each 5-minute time period within the scan period. FIG. 1 shows a sample tabular display of these six measurements accumulated at 5-minute intervals in window 102. FIG. 2 shows a sample graphical display of the number of qualified intervals accumulated at 5-minute intervals in window 202.

In addition to generating these six measurements for each time period, the HRV system calculates these six measurements plus three additional measurements for a user-defined region of the scan period. The three additional region measurements are:

1. the mean of the standard deviation of the interval times for 5-minute time periods (SD);
2. the standard deviation of the mean interval times for 5-minute periods (SDANN); and
3. the number of triplets whose difference exceeds a user-specified difference margin.

The calculation of these three region measurements is described below in detail. The HRV system allows the user to specify which portions of the scan period are to be included within the region. The user may specify that the entire scan period is to be included in the region (the default) or that any number of ranges of minutes may be included in or excluded from the region. For example, a user may select to include only sleeping hours within the region. FIG. 1 shows a sample display that includes region summary statistics for the currently defined region in window 103.

To generate the statistical data, the HRV system first calculates the beat intervals within the beat data. A beat interval is the time between two successive heart beats as preferably measured at the R component of successive QRS signals. A qualified interval is a beat interval that has an interval time which is between a user-specified minimum and maximum time and is a beat interval that is not within a user-specific number of intervals of an atrial or ventricular ectopic beat. These interval qualifications allow a user to filter out the effects of spurious intervals from the statistical measurements. For measurement purposes, an interval is considered to be within the minute in which the trailing beat occurs. FIG. 3 shows a sample display for input of the user-specified interval qualifications at window area 301.

The HRV system also detects triplets within the beat data. A triplet comprises two beat intervals that share a common beat, two consecutive beat intervals. A qualified triplet comprises two consecutive qualified intervals. For measurement purposes, a triplet is considered to be within the minute in which the trailing interval is within. FIG. 3 shows a sample display for input of the user-specified difference margin at window area 303. For every consecutive pair of qualifying intervals (that is, qualifying R-R-R triplets as measured from the R component of a QRS signal), the interval difference is the absolute value of the difference between the two intervals. The HRV system uses the qualifying triplets to calculate the RMSSD. The HRV system calculates %RRxx based on the percentage of interval differences greater than a user-specified difference margin.

The HRV system also allows the user to specify the minimum number of qualified intervals and the minimum number of qualified triplets which each 1-minute period of data must have. Minutes with a number of qualified intervals or a number of qualified triplets that is less than the user-specified minimum number will not be used in calculating the time period and region measurements. This minute qualification allows a user to filter out the effects of minutes without representative data. FIG. 3 shows a sample display for input of the user-specified minimum number of intervals and triplets per minute at window area 302.

FIG. 1 shows a sample display of statistical data in tabular format in a preferred embodiment. The display includes a menu list 101 and windows 102, 103, and 104. The menu list 101 includes menus Mode, Resolution, Review, Options, and Output. The menu Mode is used to select whether statistical or spectral data is to be displayed. The menu Resolution is used to select the resolution of the periods for the statistical data. In a preferred embodiment, the resolution options include 1, 5, 15, and 60 minutes. The menu Review is used to select whether the statistical data is to be displayed in tabular or graphical form. The menu options is used to change the interval qualifications and to show or hide time ranges that are excluded from the region. The menu Output is used to print the statistical data. Window 102 contains table headings 105, time period statistical data 106, and scroll bar 107. The table headings 105 identify the time period and the statistical data. The statistical data 106 includes the six time period statistical measurements. The scroll bar 107 is used to scroll statistical data, for time periods currently not displayed, into view. Window 103 contains summary statistics for the time ranges included within the region. Window 104 allows the user to specify which time ranges are to be included and excluded from the region.

The HRV system of the present invention allows the user to specify which portions of the scan period data are to be included in the region. The user specifies which time ranges are to be included and excluded from a region. Initially, the entire scan is included within the region. The user uses window 104 to specify the time ranges to include in or exclude from the region. The user enters a time range in boxes 110 and 111. The user selects the include button 114 or the exclude button 115 to include or exclude the entered range. The scan start button 112 and scan end button 113 allow the user to conveniently select the first or last minute of the scan period. The user can specify a particular time range by first excluding the entire scan (by selecting the start scan button, the end scan button, and the exclude button), specifying the particular time range, and selecting the include button.

In a preferred embodiment, window 103 provides summary statistics for the time ranges within the region. As the user includes or excludes time ranges from the region, the system updates the data in window 103. Also, the included data is displayed in black and the excluded data, when displayed, is displayed in gray. The menu options allows the user to select whether to display data for the excluded time ranges.

A time period may consist of both included and excluded minutes. In tabular review mode, if a time period consists of included and excluded minutes, then the time period is displayed in two rows corresponding to the included (shown in black) and the excluded (shown in gray) ranges. In graphical review mode, the included and excluded ranges are represented by two bars corresponding to the included (black) and the excluded (gray) ranges.

The system of the present invention displays the six statistical measurements for each user-selected time period. Referring to FIG. 1, the column entitled "Qualified Intervals" contains the number of qualified intervals within the corresponding time period. The column entitled "Mean Interval" contains the average interval time of the qualified intervals within the time period. The column entitled "Standard Deviation" contains the standard deviation of the interval times of the qualified intervals within the time period. The column entitled "Qualified Triplets" contains the number of qualified triplets within the time period. The column entitled "RMSSD" is the root mean square of successive differences of the qualified triplets within the time period. The column entitled "%RRxx" is a percent of triplets which exceed the user-specified difference margin within the time period. When displayed, the xx is replaced by the user-specified difference margin. For example, if the user specifies the different margin of 50 milliseconds, then the system displays "%RR50" as the column heading.

The HRV system also accumulates nine statistical region measurements. Again referring to FIG. 1, window 103 displays the region measurements. Six of the region measurements correspond to the six time period measurements and have the same identifying text as the column headings for the time period data. The data identified by "SD" contains the mean of the standard deviation of the interval times for 5-minute time periods. The data identified by "SDANN" contains the standard deviation of the mean interval times for 5-minute time periods. The data identified by "RR50" contains the number of triplets within the region whose interval time difference exceeds the user-specified difference margin.

FIG. 2 shows a sample display of statistical data in graphical format. The system displays a graph of the various measurements in window 202. Associated with window 202 are vertical scroll bar 205 and horizontal scroll bar 206. Vertical scroll bar 205 allows the user to select which of the six statistical measurements to display in window 202. Horizontal scroll bar 206 allows the user to select which time periods to display in window 202.

If a minute of ECG data has less than the user-entered minimum number of qualified intervals or minimum number of qualified triplets, then the data is not used to generate statistical data (unqualified minute). Period data represents the accumulation of statistical data for the minutes that have the minimum number of qualified intervals and triplets. In tabular review mode, periods which do not have any minutes with the minimum number of qualified intervals have a dash in the mean interval and standard deviation columns. In tabular review mode, periods which do not have any minutes with the minimum number of qualified triplets have a dash in the RMSSD and %RRxx columns. In graphical review mode, no data is graphed for periods which consist entirely of unqualified minutes. The HRV system provides a menu Scale when in graphical mode which allows the user to select a scaling factor for the graphs that are displayed and printed.

SPECTRAL DATA INTERFACE

Figure 4:
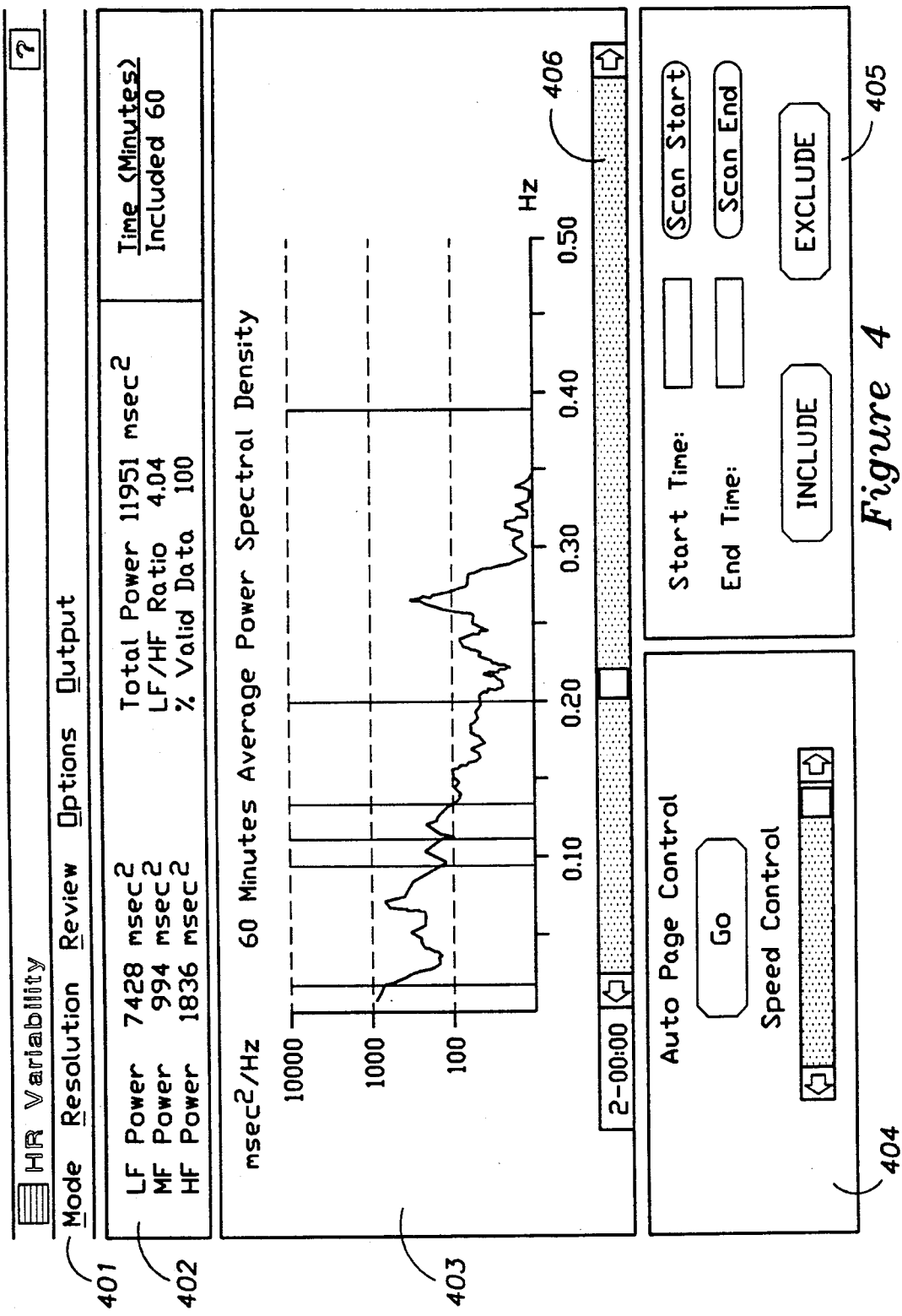
FIG. 4 shows a sample display of HRV power spectral density data for a 60-minute time period.
Figure 5:
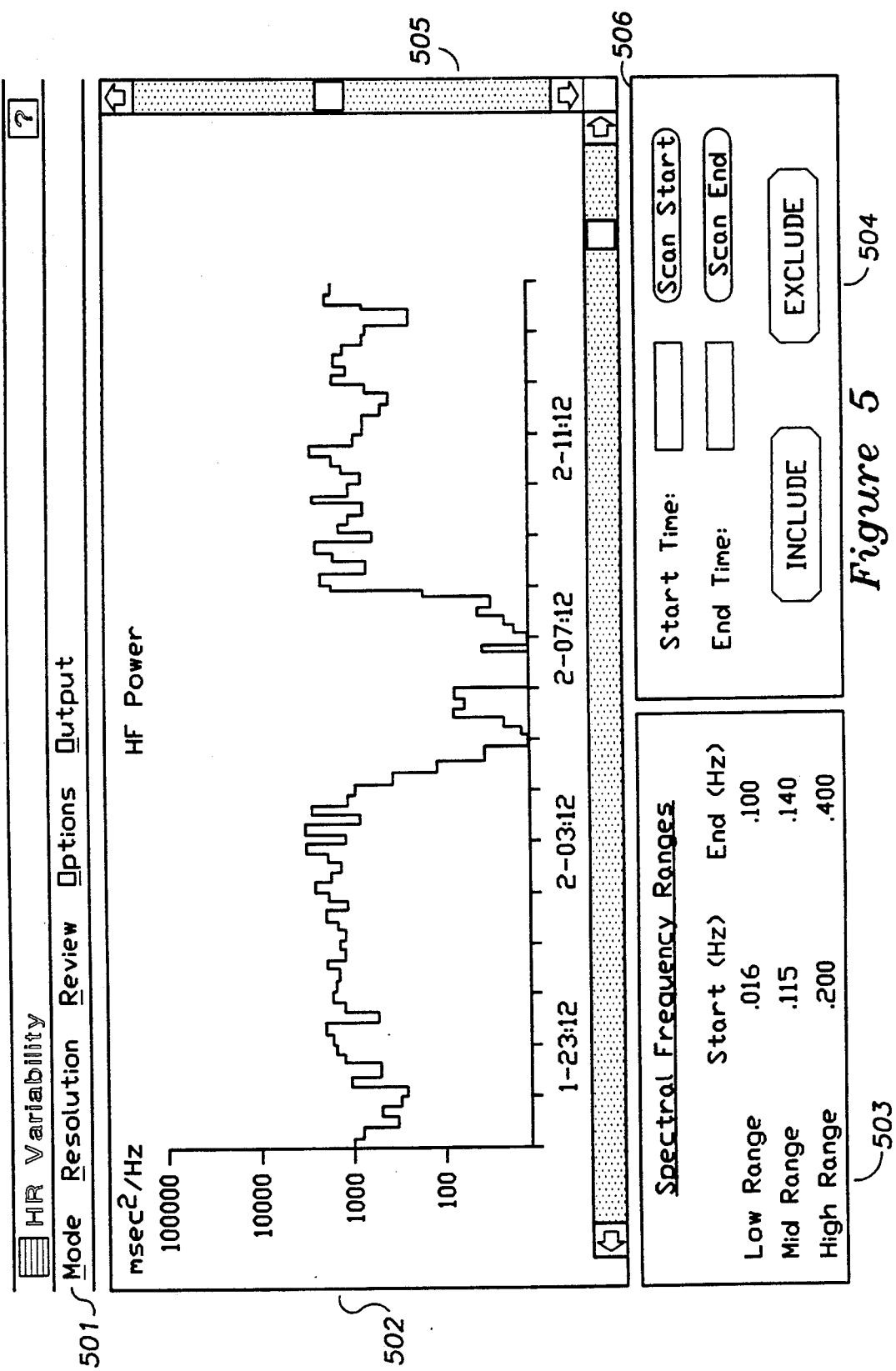
FIG. 5 shows a sample display of total high-frequency power versus time for a 12-minute time period.

The HRV system accumulates power spectral density (PSD) data for each user-specified time period within the scan period of beat data. The PSD data indicates the relative strength of rhythm patterns over a continuum of interval times. The PSD data is generated using a Fast Fourier Transform (FFT). The HRV system allows the user to specify the time base for the FFT (e.g., 2 or 4 minutes). The HRV system generates spectral data for each time base in the scan period. The HRV system also allows the user to specify the time period for accumulating PSD data. For example, the user may select a 4, 12, 20, or 60-minute time period when a 4-minute time base is specified, a 2, 10, 30, or 60-minute time period when a 2-minute time base is specified, or may select to accumulate all the data in a scan period from the current time position to the end of the scan period. FIG. 4 shows a sample display of power spectral density data for a 60-minute time period. FIG. 5 shows a sample display of total high-frequency power for each 12-minute time period.

The HRV system also allows the user to specify low-frequency, mid-frequency, and high-frequency power ranges for the spectral data. The HRV system accumulates the total power for each of the ranges for each time period.

The HRV system allows the user to specify the region for which spectral summary data is accumulated. The time ranges for the region are specified in the same manner as the ranges for the statistical portion of the HRV system. The HRV system accumulates six region spectral measurements. The region spectral measurements are:

1. the total low-frequency power;
2. the total mid-frequency power;
3. the total high-frequency power;
4. the total power;
5. the ratio of total low-frequency power to total high-frequency power; and
6. the percent of valid data.

The calculation of these measurements is described below in detail.

To generate the spectral data, the HRV system first calculates the beat intervals within the beat data using user-specified qualifications as described above for the statistical portion. The HRV system treats nonqualifying intervals by extending the previously qualified interval by the length of time in the nonqualifying interval. Thus, the time of a nonqualifying interval is added to a previous qualifying interval. The HRV system tracks the amount of time in the qualifying and nonqualifying intervals and excludes from spectral processing any time base (2 or 4-minute) (an invalid time base) that has less than a user-specified percentage of qualifying interval time (valid data).

FIG. 4 shows a display of average power spectral density (PSD) data for one time period. The display contains menu list 401 and windows 402, 403, 404, and 405. Window 403 contains the average PSD graph for one period of data. The X-axis is frequency, and the Y-axis is power (msec$^2$/Hz). The vertical lines through the graph identify the low-frequency, mid-frequency, and high-frequency ranges. The window 403 contains horizontal scroll bar 406 to allow the user to scroll into view the graph for the next time period. Window 404 allows the user to control the speed at which the graphs are automatically scrolled on the display. When the user selects the start button, the system sequentially displays the graphs for each time period until the end of the scan is reached or until the button is again selected. The speed control bar allows the user to control the speed at which the graphical data is displayed. The HRV system loops displaying a time period of PSD data, erasing the data, calculating the PSD data for the next time period, and displaying the newly calculated PSD data. Window 402 contains spectral summary data for the user-specified region. The spectral data includes the total average power in the low-, mid-, and high-frequency ranges, the total power between 0.016 and 0.5 hertz, the ratio of total low-frequency power to total high-frequency power, the percentage of valid data within the valid time bases within the region of the displayed time period, and the total number of minutes within the valid time bases of the displayed portion of the region.

The menu list 401 contains menus Mode, Resolution, Review, Options, and Output. The menu Mode is used to select whether spectral or statistical data is to be displayed. The menu Resolution allows the user to select the resolution at which to accumulate the PSD data. If the accumulation is performed with a 2-minute time base, then the resolution selections are 2, 10, 30, and 60 minutes or all. If the accumulation is performed with a 4-minute time base, the resolution selections are 4, 12, 20, and 60 minutes or all. The menu Review is used to select whether total power spectral data for the spectrum of frequencies for a time period or total power data over time for a frequency range are to be displayed. The menu options allows the user to change the interval qualifications, the time base, or the frequency ranges.

Figure 6:
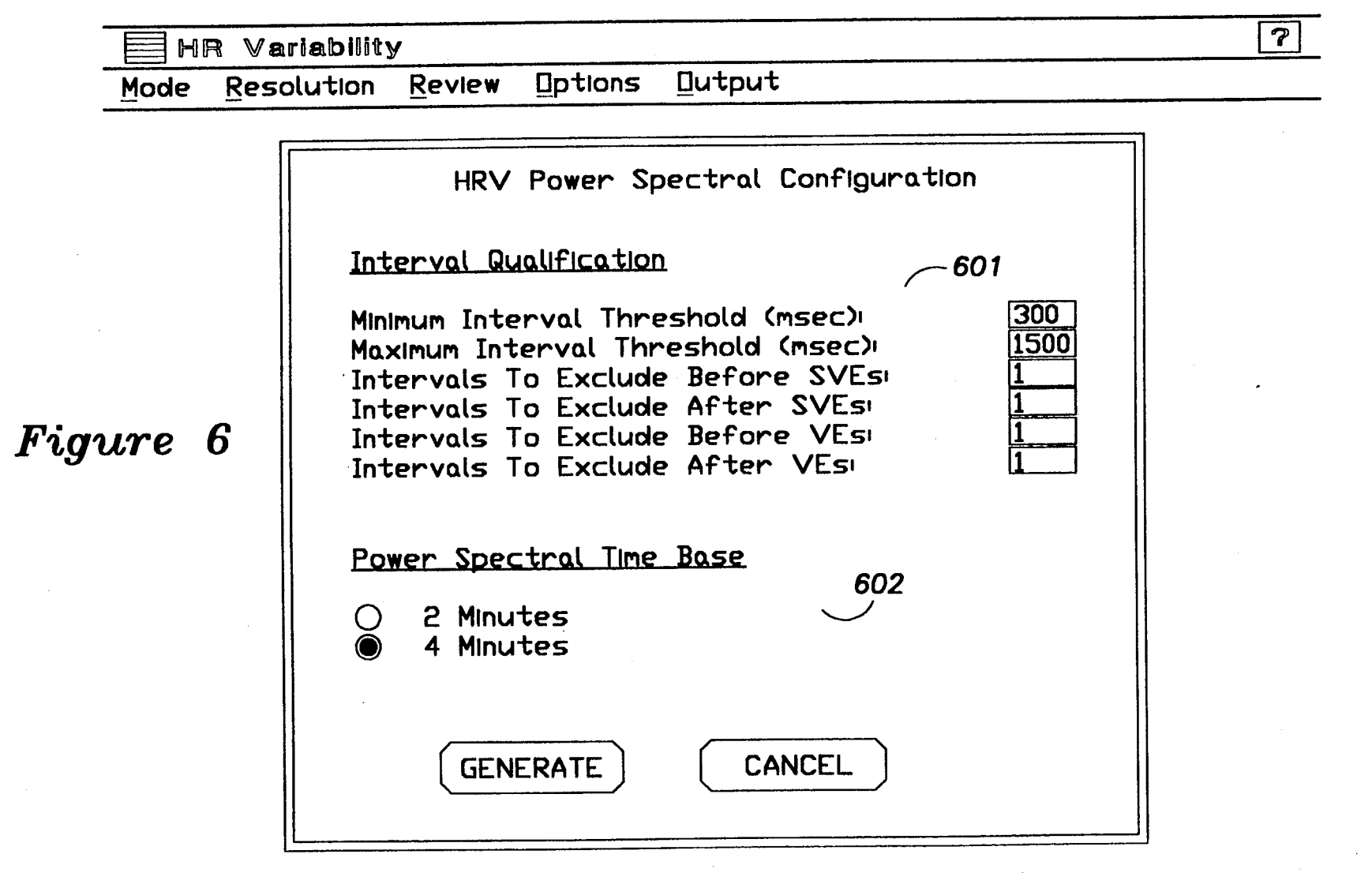
Figure 7:
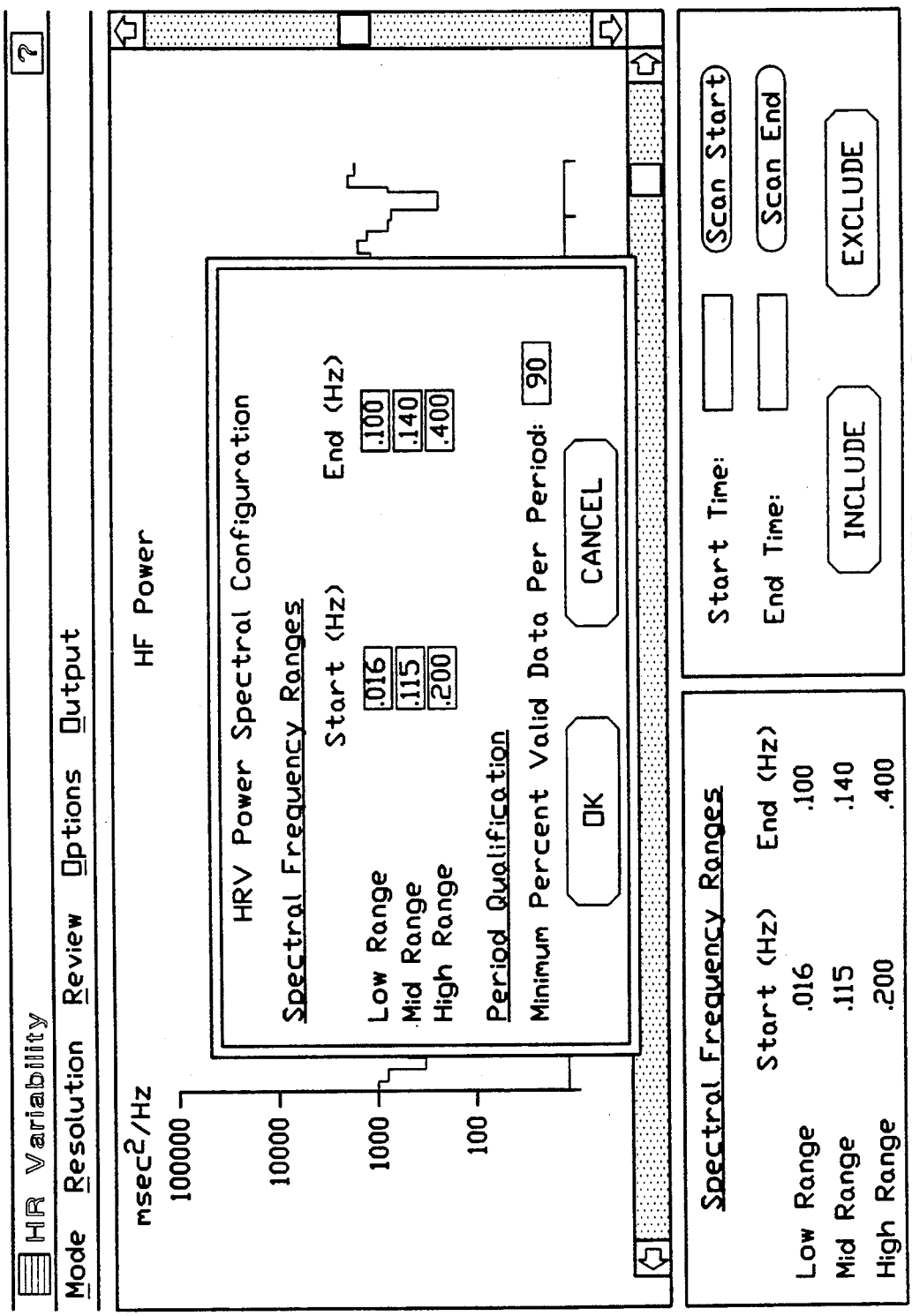
FIG. 7 shows a sample display for input of user-specified frequency ranges and period qualifications for spectral analysis.

FIG. 5 shows a sample power analysis graph. The display contains menu list 501, and windows 502, 503, and 504. Window 502 displays power analysis graphs for the low-frequency, mid-frequency, high-frequency, and total frequency power, and the ratio of total low-frequency power to total high-frequency power. The X-axis is time, and the Y-axis is power (resec$^2$/Hz). Window 502 includes horizontal scroll bar 506 and vertical scroll bar 505. Vertical scroll bar 505 is used to select the particular frequency range to be displayed. Horizontal scroll bar 506 is used to scroll a particular time period into view. Window 503 displays the currently selected frequency ranges, and window 504 is used to specify the region. Data from excluded time ranges, when displayed, is preferably displayed in gray. FIG. 6 shows a sample display of an input window for interval qualifications and the time base. Window area 601 allows the user to input interval qualifications. Window area 602 allows the user to input time base data. FIG. 7 shows sample display of an input window for the frequency ranges and period qualifications.

For either statistical or spectral data, the HRV system prints a variety of reports based on the user-specified qualifications, resolution, time bases, time periods, regions, and menu selections.

STATISTICAL PORTION

Figure 9:
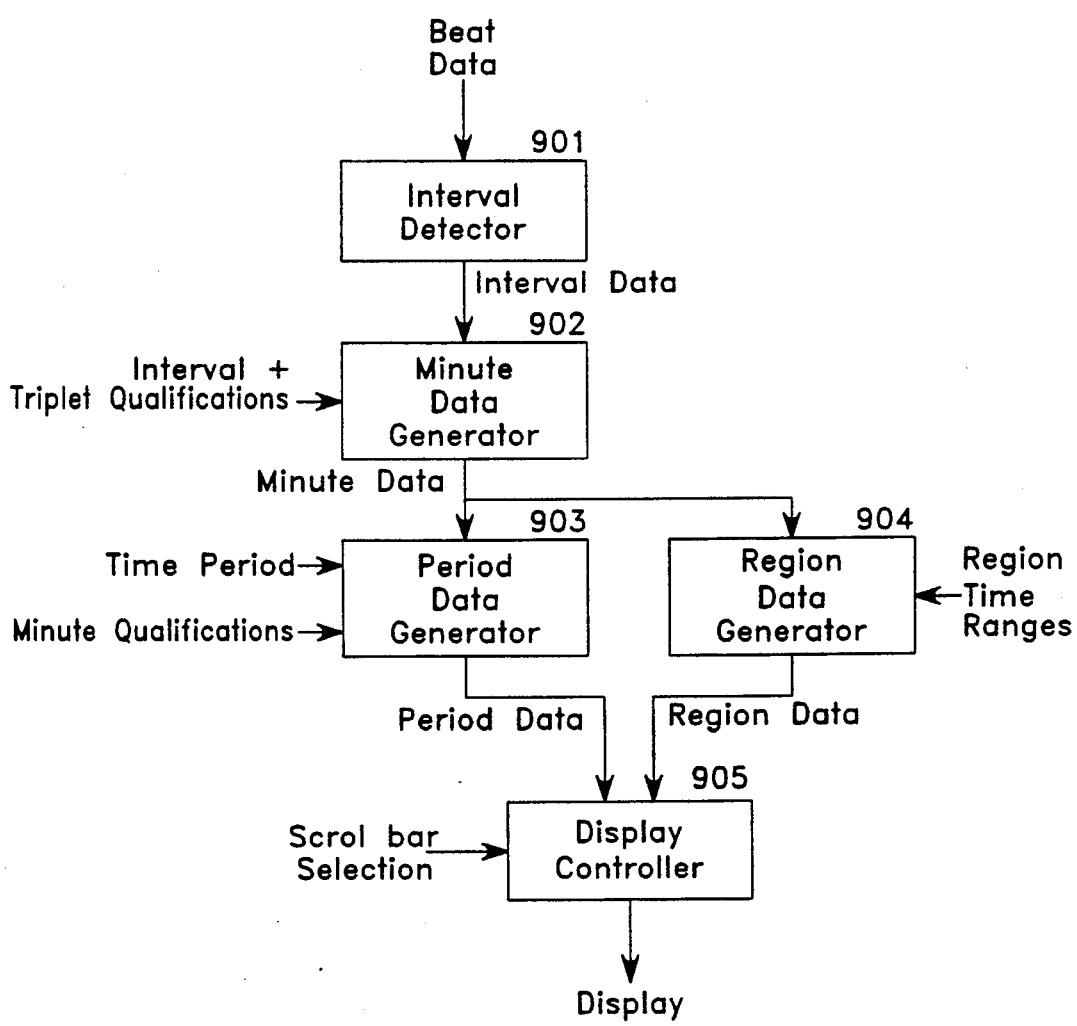
FIG. 9 is an overview schematic diagram of the components for the statistical portion of the HRV system.

FIG. 9 is an overview schematic diagram of the components for the statistical portion of the HRV system. The statistical portion comprises interval detector 901, minute data generator 902, period data generator 903, region data generator 904, and display controller 905. The interval detector 901 inputs the beat data for the entire scan period and outputs interval data. The interval data includes an array of interval times for the beats detected in the beat data. The minute data generator 902 inputs interval data and the user-specified interval and triplet qualifications, and generates and outputs minute data. The minute data is an array with an entry having the six statistical measurements for each minute within the scan. The period data generator 903 inputs the minute data and the user-specified time period and minute qualifications, and generates and outputs period data. The period data is an array with an entry having the six statistical measurements for each period within the scan. The region data generator 904 inputs the minute data and the user-specified region time ranges, and generates and outputs region data. The region data is the nine region statistical measurement for the user-specified region. The display controller 905 inputs the period and region data and the user-specified scroll bar selection, and controls the display of the statistical data in tabular or graphical format.

FIGS. 10 through 19 are flow diagrams of methods implementing the statistical portion of the HRV system in one embodiment. One skilled in the art would appreciate that these flow diagrams provide an overview of the structure of a computer program implementing the methods of the present invention. Table 1 contains a definition of representative data structures for the representative statistical portion.

TABLE 1

M[]

| | |
|---|---|
| M.IntervalCount | number of qualified intervals within the minute |
| M.IntervalSum | sum of the intervals times within the minute |
| M.IntervalSqSum | sum of the square of the interval times within the minute |
| M.TripletCount | number of qualified triplets within the minute |
| I.TripletDiffSqSum | sum of the square of the differences of the interval times of triplets within the minute |
| M.RRxx | number of triplets whose difference in interval times exceeds the difference margin within the minute |

P[]

| | |
|---|---|
| P.QualifiedIntervals | number of qualified intervals within the period |
| P.IntervalSum | sum of the interval times within the period |
| P.IntervalSqSum | sum of the square of the interval times within the period |
| P.QualifiedTriplets | number of qualified triplets within the period |
| P.TripleDiffSqSum | sum of the square of difference of the interval times of triplets within the period |
| P.RRxx | number of triplets whose difference in interval times exceeds the difference margin within the period |
| P.MeanInterval | average interval time of the intervals within the period |
| P.SD | standard deviation of the interval times of the intervals within the period |
| P.RMSSD | root mean square of the sum of successive differences of triplets within the period |
| P.%RRxx | percentage of triplets whose difference in interval times exceeds the difference margin within the period |

R[]

TABLE 1-continued

| | |
|---|---|
| R.QualifiedIntervals | number of qualified intervals within the region |
| R.MeanIntervalSum | sum of the interval times within the region |
| R.SDSum | sum of the standard deviations of the interval times of the intervals within the region |
| R.MeanIntervalSqSum | sum of the square of the average interval times within the region |
| R.QualifiedTriplets | number of qualified triplets within the region |
| R.RRxx | number of triplets whose difference in interval times exceeds the difference margin within the region |
| R.%RRxxSum | sum of the percentage of triplets whose difference in interval times exceeds the difference margin within the region |
| R.MeanInterval | average interval time of the intervals within the region |
| R.SD | standard deviation of the interval times of the intervals within the region |
| R.SDANN | see spectral data portion |
| R.RMSSD | root mean square of the sum of successive differences in triplets within the region |
| R.%RRxx | percentage of triplets whose difference in interval times exceeds the difference margin within the region |

Figure 10:
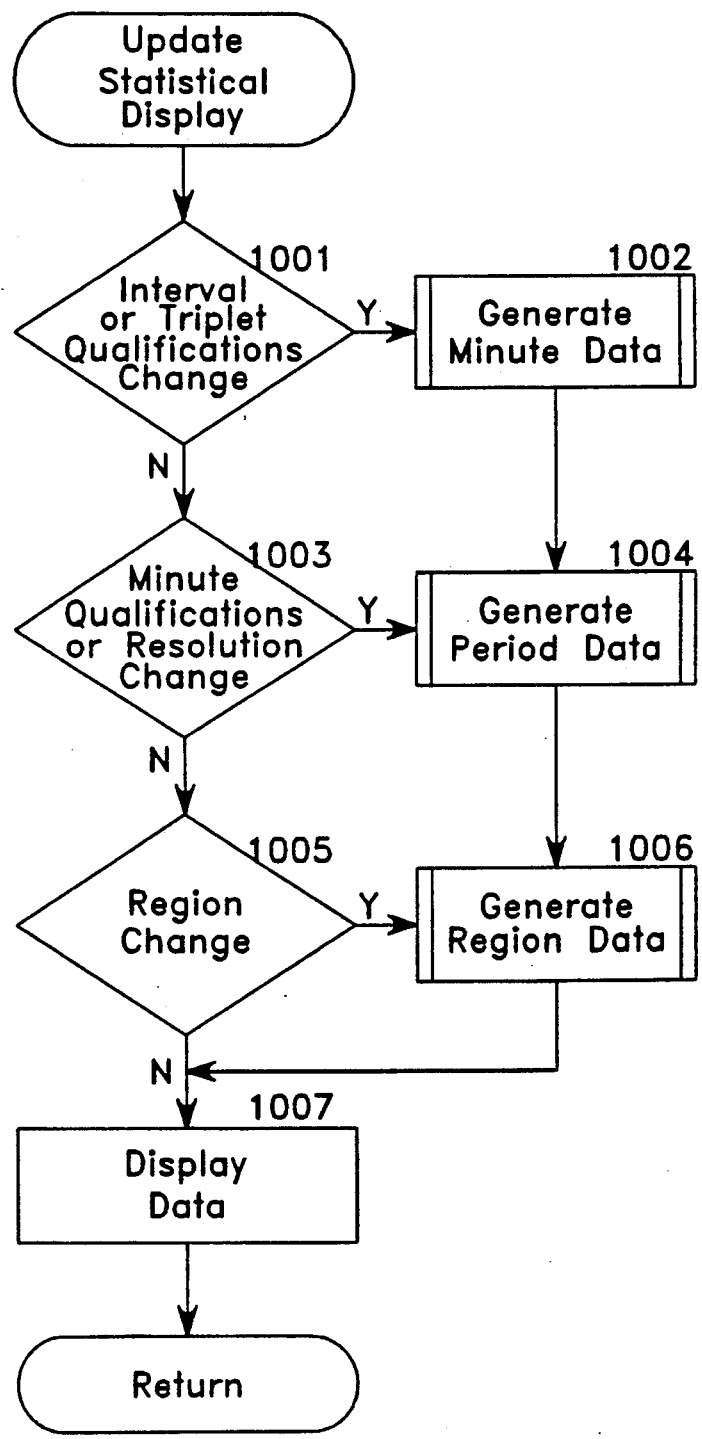
FIG. 10 is a flow diagram of the routine UpdateStatisticalDisplay.

FIG. 10 is a flow diagram of the routine UpdateStatisticalDisplay. This routine receives the user-specified interval and triplet qualifications, minute qualifications, time period, region time ranges, scroll bar selection, and displays the statistical data. In step 1001, if the interval or triplet qualifications have changed, then the routine continues at step 1002, else the routine continues at step 1003. If the interval or triplet qualifications have changed since the minute data was last generated, then the minute data needs to be regenerated. In step 1002, the routine invokes routine GenerateMinuteData. In step 1003, if the time period or minute qualifications have changed, then the routine continues at step 1004, else the routine continues at step 1005. If the time period or minute qualifications have changed, then the period data needs to be regenerated. In step 1004, the routine invokes routine GeneratePeriodData. In step 1005, if the region has changed, then the routine continues at step 1006, else the routine continues at 1007. If the region has changed since the last region data was generated, then the region data is regenerated. One skilled in the art would appreciate that certain optimization would reduce the regeneration of data, for example, if only the time period changes, then the region data may not need to be regenerated In step 1006, the routine invokes routine GenerateRegionData. In step 1007, the routine displays the updated data. The display of the data takes into consideration whether the data is to be displayed in tabular format or graphical format, and whether the excluded period data is to be hidden or shown. The routine then returns.

Figure 11:
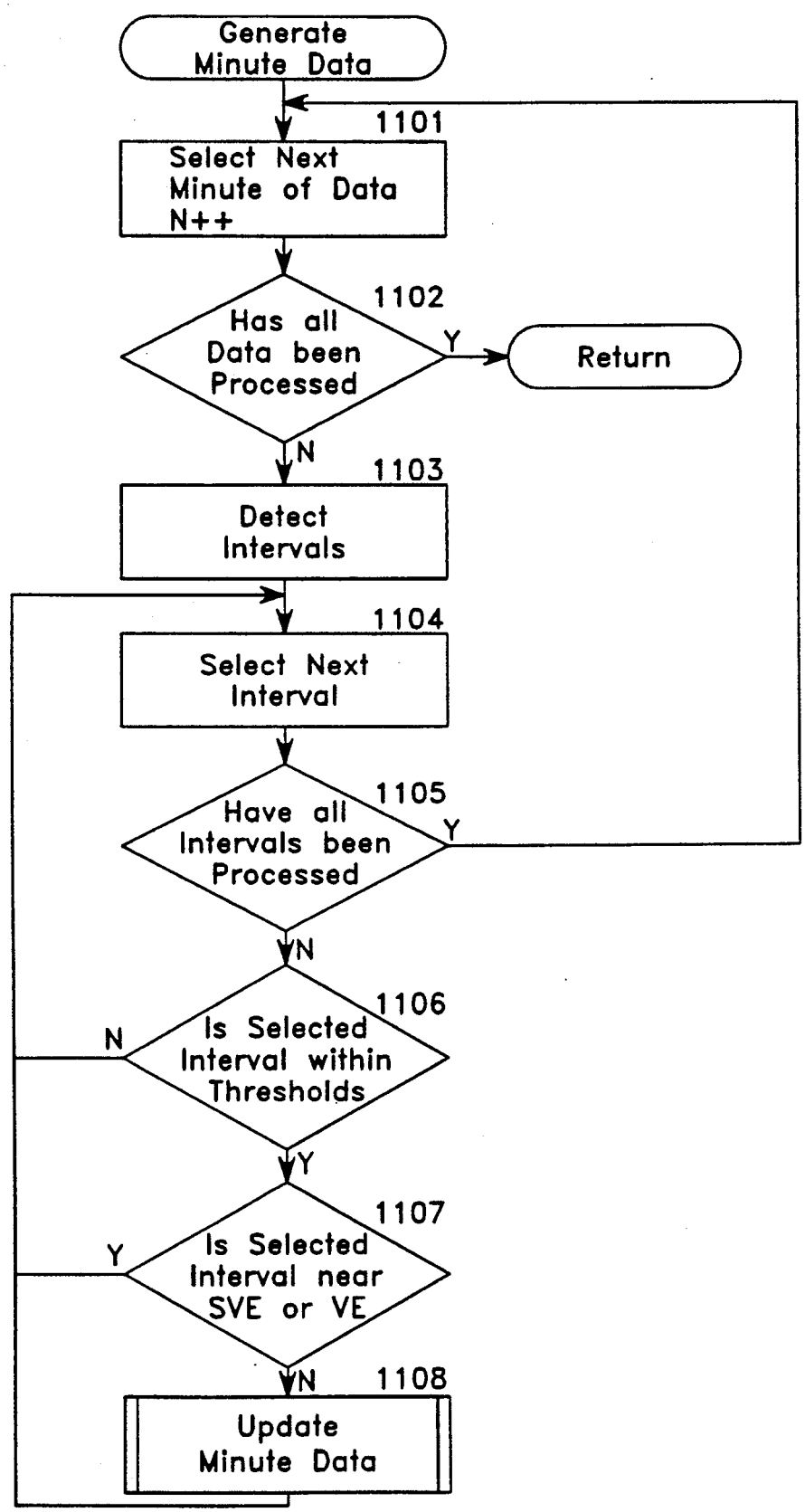
FIG. 11 is a flow diagram of the GenerateMinuteData routine.

FIG. 11 is a flow diagram of the GenerateMinuteData routine. This routine receives an annotated beat list and generates the minute data. This routine corresponds to the interval detector 901 and the minute data generator 902. The minute data is stored in array M, which has one entry f or each minute of data in the scan. In step 1101, the routine selects the next minute of beat data starting with the first minute of data and increments index n. Index n is an index into the array M and indicates the currently selected minute within the scan period. In step 1102, if all the beat data has been processed, then the routine returns, else the routine continues at step 1103. In step 1103, the routine detects beat intervals in the selected minute of beat data. One skilled in the art would appreciate that any of various well-known techniques for determining beat intervals may be used. This step corresponds to interval detector 901. One skilled in the art would also appreciate that the interval data need only be generated once for each scan of beat data because none of the user-specified parameters affect the interval data detection process. In steps 1104 through 1108, the routine loops processing each interval within the selected minute of data. The routine determines whether the intervals meet the interval and triplet qualifications and updates array M. In step 1104, the routine selects the next interval within the selected minute of data. In step 1105, if all the intervals within the selected minute have been processed, then the routine loops to step 1101 to select the next minute of beat data, else the routine continues at step 1106. In step 1106, if the selected interval is within the minimum and maximum interval qualifications, then the routine continues at step 1107, else the selected interval is disregarded and the routine loops to step 1104 to select the next interval. In step 1107, if the selected interval is within the user-specified proximity of either an atrial or ventricular ectopic beat, then the selected interval is disregarded and the routine loops to step 1104 to select the next interval, else the routine continues at step 1108. In step 1108, the routine invokes routine UpdateMinuteData and then loops to step 1104 to select the next interval.

Figure 12:
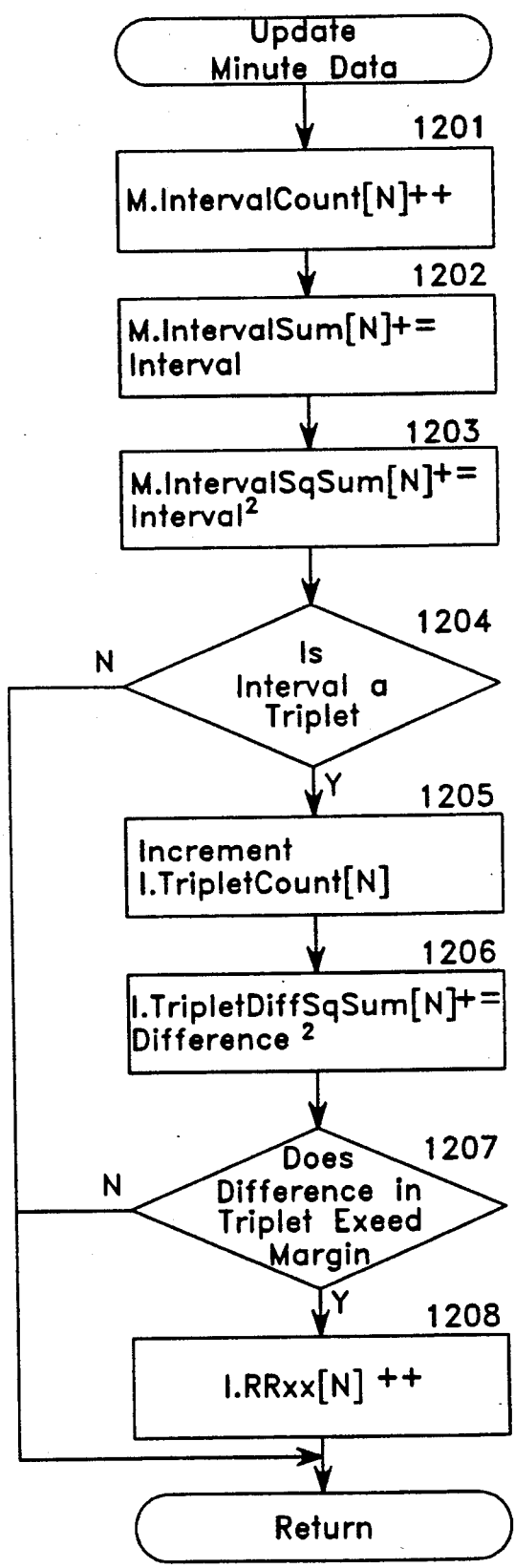
FIG. 12 is a flow diagram of the routine UpdateMinuteData.

FIG. 12 is a flow diagram of the routine UpdateMinuteData. This routine updates the statistical information in array M for the currently selected minute (index n in the invoking routine) with the currently selected interval. If there are no qualifying intervals within the selected minute, then this routine is not invoked and the values in array M f or index n are zero. In step 1201, the routine increments the interval count f or the selected minute. In step 1202, the routine adds the interval time for the selected interval to the sum of interval times for qualifying intervals within the selected minute. In step 1203, the routine adds the square of the interval time f or the selected interval to the sum of the squares of the interval times for the qualifying intervals within the selected minute. The sum of the squares is used to determine the standard deviation for the time periods. In step 1204, if the selected interval is part of a triplet, the routine continues at step 1205, else the routine returns. In step 1205, the routine increments the count of the number of triplets for the selected minute. In step 1206, the routine adds the square of the difference between the interval times of the triplet to the sum of the squares of the difference between the interval times of the triplets within the selected minute. In step 1207, if the difference between the interval times of the triplet exceeds a user-defined difference margin, then the routine continues at step 1208, else the routine returns. In step 1208, the routine increments a count of the triplets that exceed the difference margin for the selected minute, and the routine then returns.

Figure 13:
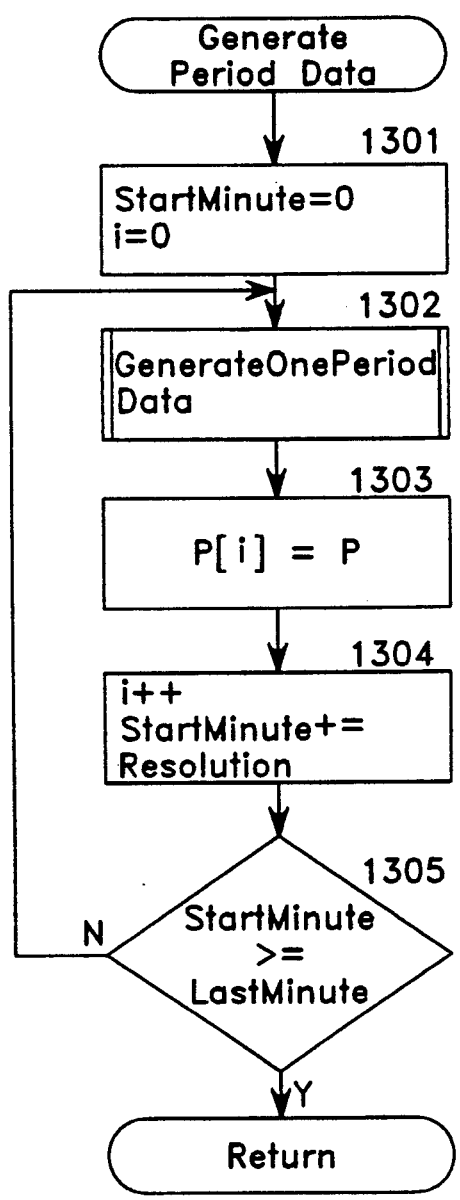
FIG. 13 is flow diagram of routine GeneratePeriodData.

FIG. 13 is flow diagram of routine GeneratePeriodData. This routine receives minute data and accumulates period data for the entire scan period. The routine inputs the minute data stored in array M and outputs the period data in array P. In step 1301, the routine initializes variable StartMinute to zero and index i to zero. Index i is an index into array P, which contain an entry for each time period in the scan period. In steps 1302 through 1305, the routine loops, generating the data for each time period and storing the data in array P. In step 1302, the routine invokes routine GenerateOnePeriodData, which calculates the statistical data for the selected time period and returns the data in scalar structure P. In step 1303, the routine sets the entry i in array P to the values in structure P. In step 1304, the routine increments index i and adds the number of minutes in the resolution (time period) to the variable StartMinute to indicate the next time period. In step 1305, if variable StartMinute is greater than or equal to the last minute of data in the minute data, then the routine returns, else the routine loops to step 1302 to generate the data for the next time period.

Figure 14:
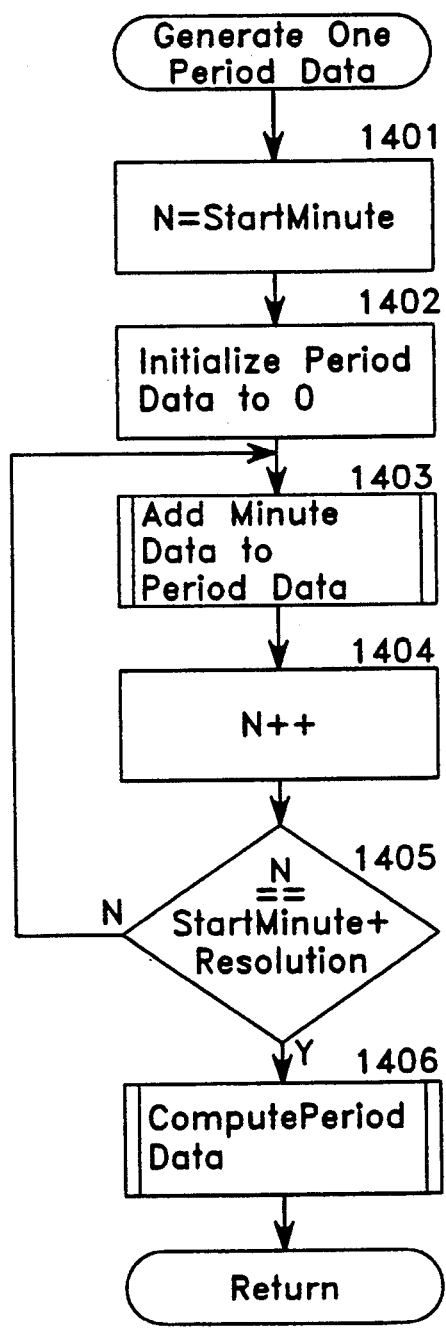
FIG. 14 is a flow diagram of routine GenerateOnePeriodData.

FIG. 14 is a flow diagram of routine GenerateOnePeriodData. This routine receives the index into array M, generates one period of data starting at that index, and returns the period data in structure P. In step 1401, the routine sets index n equal to variable StartMinute. Index n serves as an index into the array M. In step 1402, the routine initializes the structure P to zero. In steps 1403 through 1405, the routine loops, accumulating data for the period. In step 1406, the routine invokes routine AddMinuteDatatoPeriodData. In step 1404, the routine increments index n to point to the next entry in array M. In step 1405, if index n equals the variable StartMinute plus the number of minutes in the resolution, then the data for the period has been accumulated and the routine continues at step 1406, else the routine loops to step 1403 to accumulate the data for the next minute. In step 1406, the routine invokes routine ComputePeriodData, and the routine returns.

Figure 15:
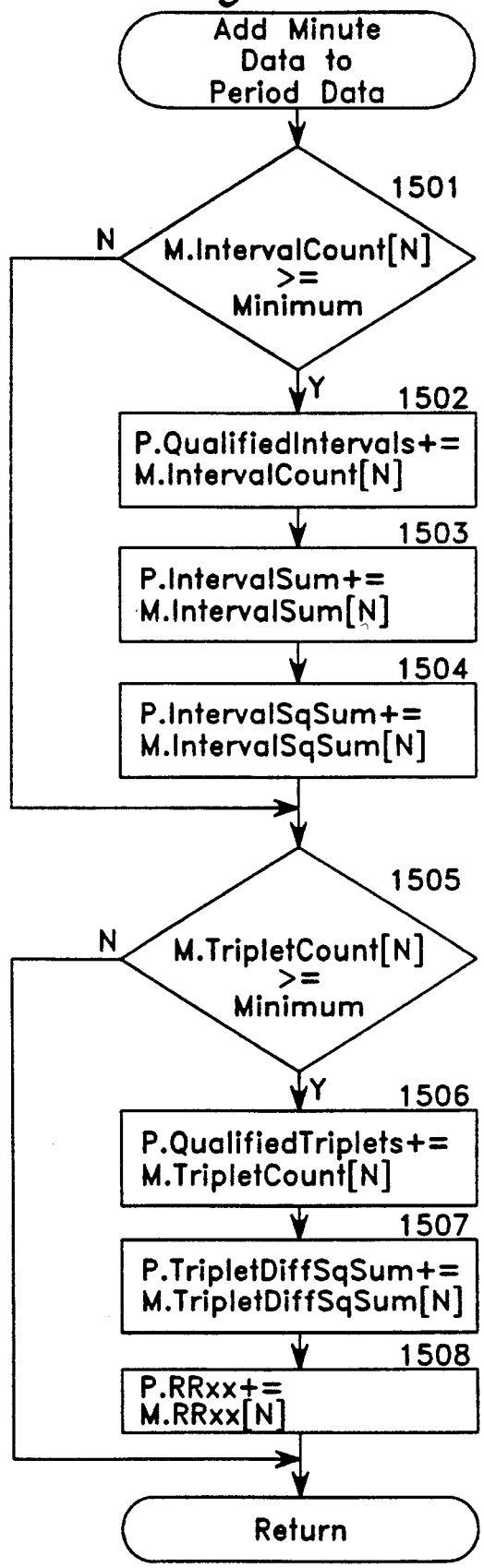
FIG. 15 is a flow diagram of routine AddMinuteDatatoPeriodData.

FIG. 15 is a flow diagram of routine AddMinuteDatatoPeriodData. This routine adds the data for a selected minute to a running total of data for a time period. The routine is passed index n, which indicates the selected minute, and the routine updates the data in structure P. In step 1501, if the number of intervals within the selected minute is greater than the user-specified minimum number of qualified intervals, then the routine continues at step 1502 to add the minute data to the period data, else the routine continues at step 1505. In step 1502, the routine adds the number of qualified intervals for the selected minute to the total number of qualified intervals for the period. In step 1503, the routine adds the sum of the interval times for the selected minute to a running total of the sum of the interval times for the period. In step 1504, the routine adds the sum of the squares of the interval times for the selected minute to a running total of the sum of the squares of the interval times for the period. In step 1505, if the triplet count for the selected minute is greater than a user-specified minimum number of qualified triplets, then the routine continues at step 1506 to add the triplet data for the selected minute to the period data, else the routine returns. In step 1506, the routine adds the number of triplets within the selected minute to a running total of the number of triplets within the period. In step 1507, the routine adds the sum of the square of the difference of the triplets within the selected minute to a running total of the sum of the squares of the differences of the triplets within the period. In step 1508, the routine adds the count of the number of triplets that exceed the difference margin within the selected minute to a running total for the period, and the routine returns.

Figure 16:
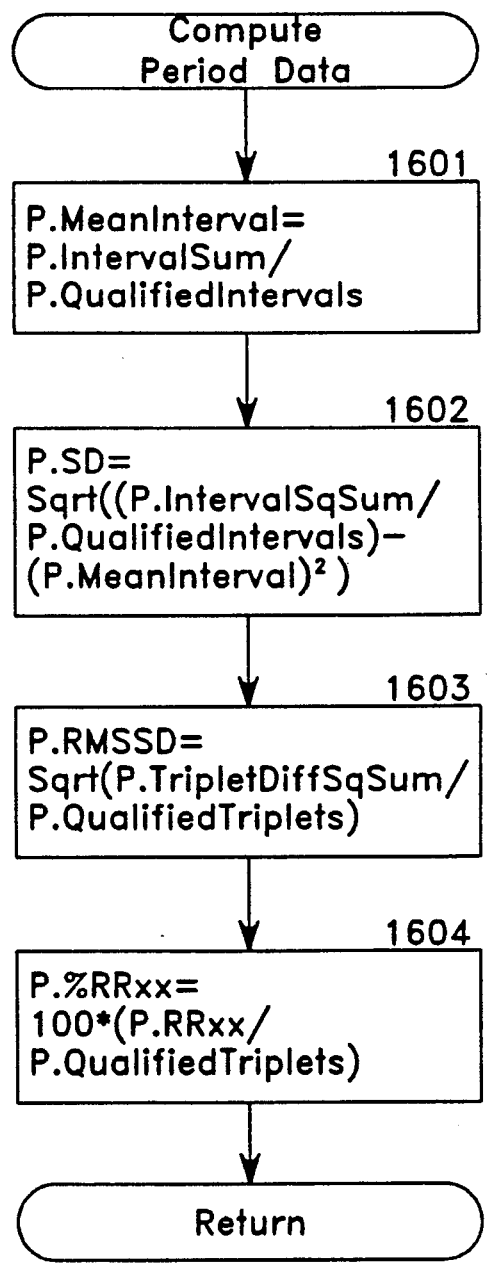
FIG. 16 is a flow diagram of routine ComputePeriodData.

FIG. 16 is a flow diagram of routine ComputePeriodData. This routine is invoked after minute data has been accumulated for a period to complete generation of the period data. This routine updates data in structure P. In step 1601, the routine calculates the mean interval time within the period. In step 1602, the routine calculates the standard deviation of the interval times within the period. In step 1603, the routine calculates the root mean square of successive differences for the triplets within the period. In step 1604, the routine calculates the percentage of triplets within the period whose interval time difference exceeds the difference margin, and the routine then returns.

Figure 17:
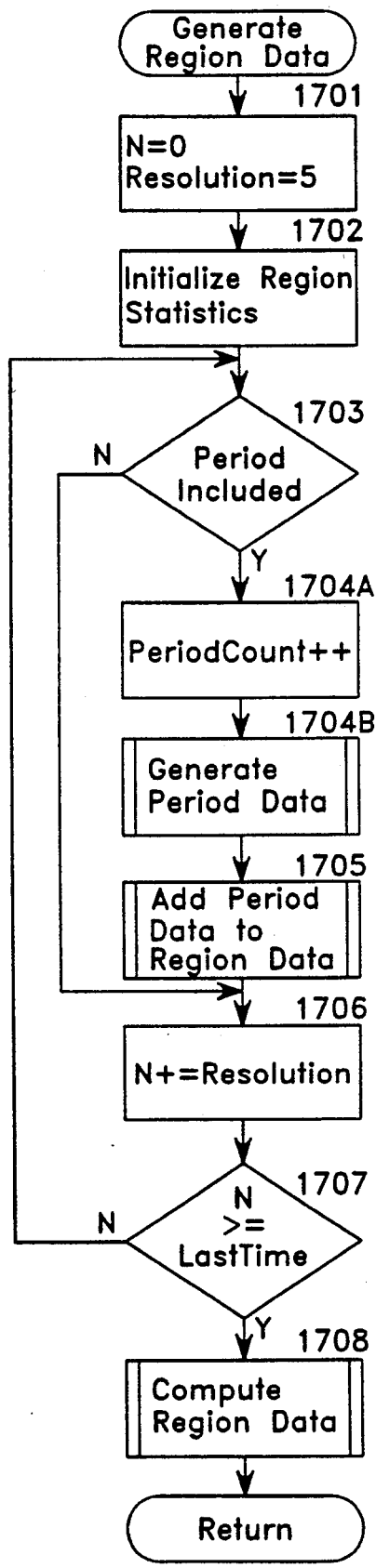
FIG. 17 is a flow diagram of routine GenerateRegionData.

FIG. 17 is a flow diagram of routine GenerateRegionData. This routine accumulates the region data for the time periods within the region. In step 1701, the routine initializes index n to zero and the resolution to 5 minutes. In a preferred embodiment, the region data is generated from 5-minute period data. Index n is used as an index into array M. In step 1702, the routine initializes the region data structure R to zero. In steps 1703 through 1707, the routine loops accumulating the region data. In step 1703, if the period starting at the minute data indexed by index n is within the region, then the routine continues at step 1704A, else the routine continues at step 1706. The method of this routine allows a period to be fully included or excluded. One skilled in the art would appreciate that a period may be partially included and excluded. In step 1704A, the routine increments the count of the number of included periods. In step 1704B, the routine invokes routine GeneratePeriodData to accumulate the minute data for 5 minutes. In step 1705, the routine invokes routine AddPeriodDatatoRegionData. In step 1706, the routine adds the number of minutes in the resolution to index n to indicate the start of the next period. In step 1707, if index n is greater than or equal to the last time of minute data, then the routine continues at step 1708, else the routine loops to step 1703 to process the next period data. In step 1708, the routine invokes routine ComputeRegionData, and the routine returns.

Figure 18:
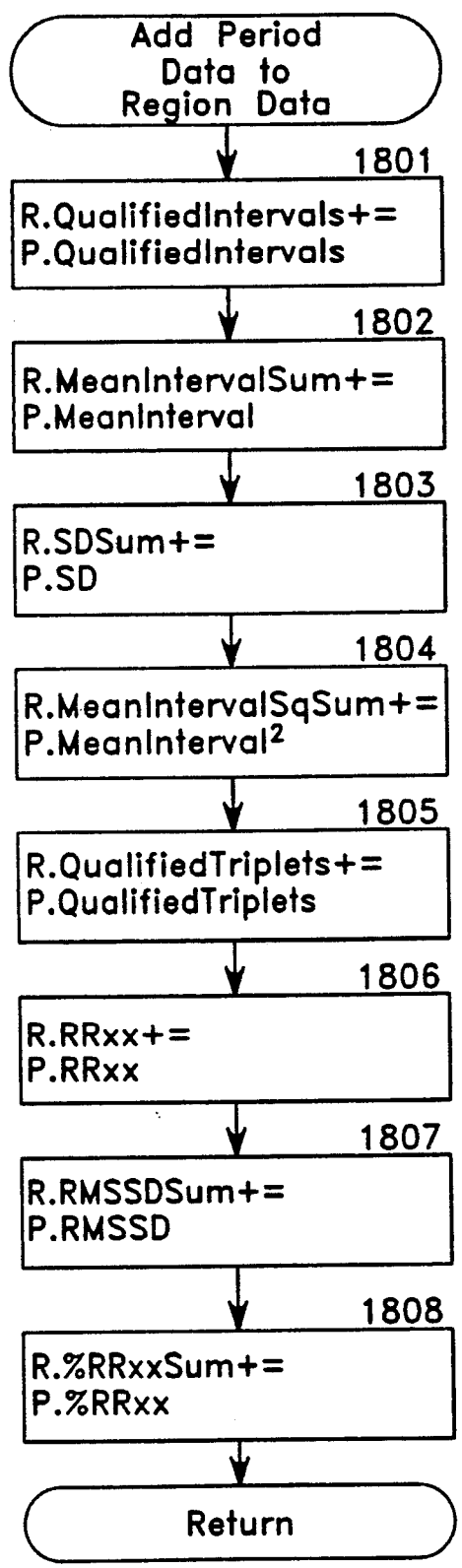
FIG. 18 is a flow diagram of routine AddPeriodDatatoRegionData.

FIG. 18 is a flow diagram of routine AddPeriodDatatoRegionData. This routine adds the accumulated data for the selected period to a running total of region data. The routine accumulates the region data in array R. In step 1801, the routine adds the number of qualified intervals within the selected period to the running total of the qualified intervals within the region. In step 1802, the routine adds the mean interval time for the selected period to the running total of the mean interval times for the region. In step 1803, the routine adds the standard deviation for the period to a running total for the standard deviation for the region. In step 1804, the routine adds the mean interval time squared for the selected period to the running total of the mean interval times squared for the region. In step 1805, the routine adds the number of qualified triplets within the selected period to a running total of the number of qualified triplets within the region. In step 1806, the routine adds the number of triplets whose difference in interval times exceeds the difference margin for the selected period to a running total for the region. In step 1807, the routine adds the root means square of successive differences for the selected period to a running total for the region. In step 1808, the routine adds the percentage of triplets that exceed the difference margin within the selected period to a running total for the region, and the routine returns.

Figure 19:
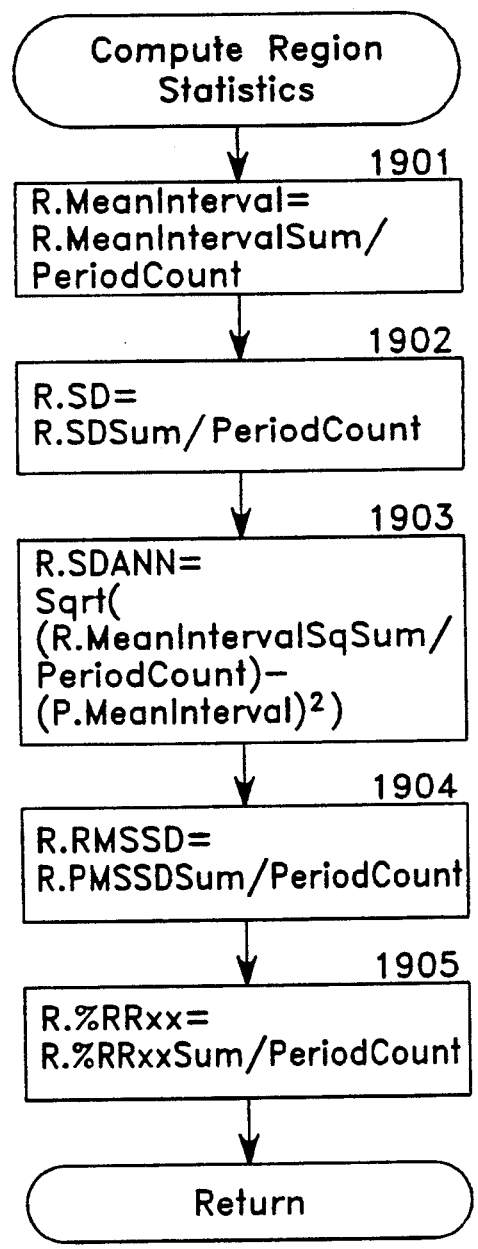
FIG. 19 is a flow diagram of routine ComputeRegionData.

FIG. 19 is a flow diagram of routine ComputeRegionData. This routine is invoked after the period statistics have been accumulated for the region to complete generating the region data. This routine updates data in structure R. In step 1901, the routine calculates the mean interval time for the region by dividing the sum of the mean interval time for the periods by the period count. In step 1902, the routine calculates the standard deviation for the region by dividing the sum of the standard deviations for the periods by the period count. In step 1906, the routine calculates the SDANN for the region. In step 1904, the routine calculates the root mean square of successive differences by dividing the total of the root mean square of successive differences for the periods by the period count. In step 1905, the routine calculates the percentage of triplets within the region that exceed the margin by dividing the sum of the percentages for the periods by the period count, and the routine returns.

SPECTRAL PORTION

Figure 20:
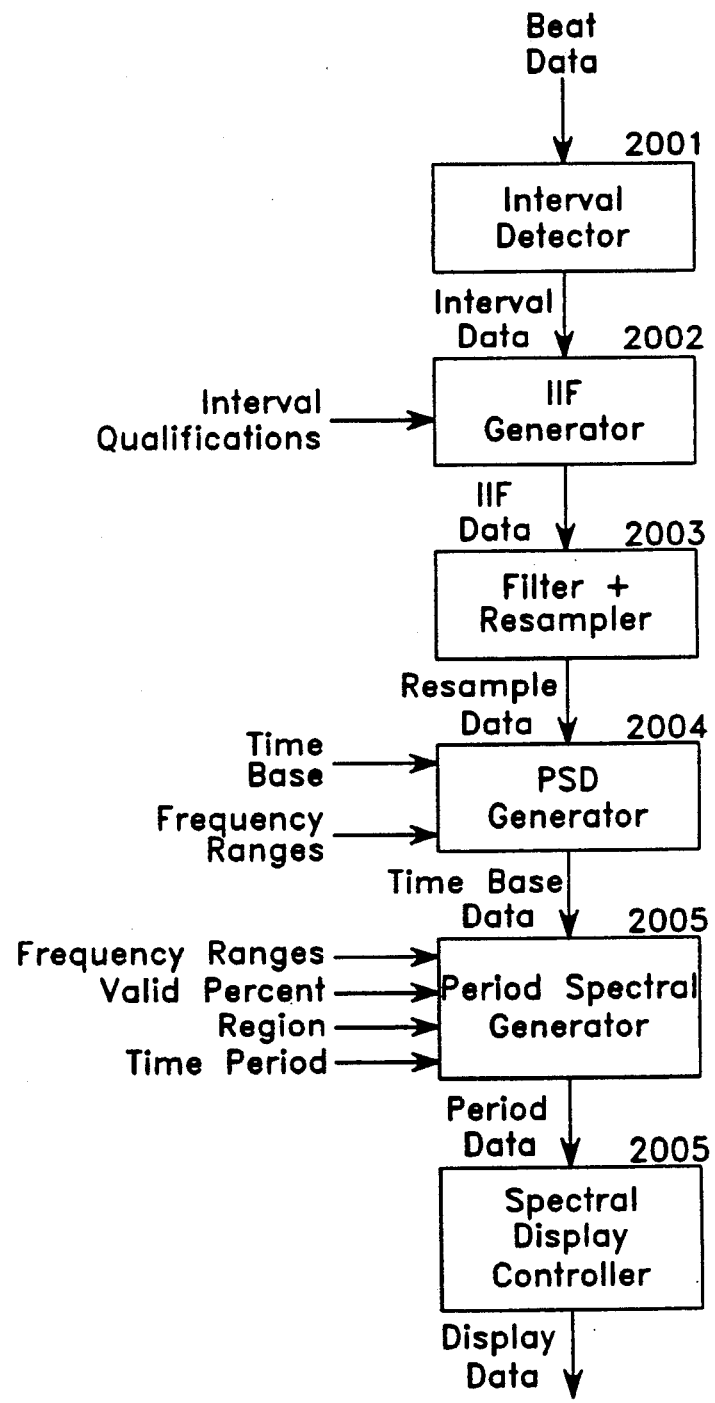
FIG. 20 is an overview schematic diagram of the components for the spectral portion of the HRV system.

FIG. 20 is an overview schematic diagram of the components for the spectral portion of the HRV system. The spectral portion comprises interval detector 2001, IIF generator 2002, filter and resampler 2003, PSD generator 2004, period spectral generator 2005, and spectral display controller 2006. The interval detector 2001 inputs the beat data for the entire scan period and outputs interval data. The interval detector is described above with reference to the statistical portion of the HRV system. The IIF (instantaneous interval function) generator 2002 inputs the interval data and output the IIF data and valid data statistics. The IIF data is an array in which each entry represents a beat interval and contains the difference in interval time from the previous interval and contains the interval time for interval. An interval that does not meet the interval qualifications is disregarded and its interval time is added to the interval time of the previous qualified interval. The interval time for nonqualifying intervals is accumulated for valid time base analysis. The filter and resampler 2003 inputs the IIF data and outputs resample data. The resample data is an array of containing the average area per millisecond of the IIF for every 250 millisecond. The filter and resampler 2003 filter the IIF data with a rectangular convolution filter of a width of 500 milliseconds. The filter generates one sample every 250 to yield resampled IIF data at 4 hertz. A resampling rate of 4 hertz is preferred because the human autonomic response is typically in the range of 0 to 1 hertz and the spectral estimate is accurate to about one-fourth this range due to the effects of filtering. The PSD generator 2004 inputs the resample data and user-specified time base and frequency ranges, and outputs the PSD data. The PSD data is an array containing PSD value for each time base in the scan period. The PSD generator 2004 uses a periodogram technique on the resample data to generate the PSD data. The PSD generator 2004 performs a Discrete Fourier Transform on the resample data for every time base in the scan. If the time base is 2 minutes, then the PSD generator uses a 512 data point Fast Fourier Transform (FFT) (480 data points at 4 hertz). If the time base is 4 minutes, then the PSD generator uses a 1024 data point FFT (960 data points at 4 hertz). The PSD generator scales the resample data with a Hanning Window to reduce spectral leakage before for the FFT is performed. The PSD generator squares, sums, and normalizes the resulting FFT component to generate the PSD values. The PSD generator also calculates the total power for the user-specified low-, mid-, and high-frequency ranges. The period spectral generator 2005 inputs the PSD data and user-specified time period, frequency ranges, time base qualifications, and region definition and outputs the period PSD data. The period PSD data is an array of the average PSD data of the time bases within each period. The period spectral generator 2005 also calculates the region measurements for each period. The spectral display controller 2006 inputs the period data and controls the display of the data.

FIGS. 21 through 28 are overview flow diagrams of the spectral portion of the HRV system. These flow diagrams represent the structure of computer programs that implement an embodiment of the present invention. Table 2 contains representative data structures used in the spectral portion of the HRV system.

TABLE 2

| IIF[] | |
|---|---|
| IIF.value | difference between the length of the current interval and the previous interval |
| IIF.length | length of the current interval |
| TB[] | |
| TB.PSD[] | array of power spectral density data of the time base |
| TB.valid | valid time within the time base |
| TB.LF | total low-frequency power within the time base |
| TB.MF | total mid-frequency power within the time base |
| TB.HF | total high-frequency power within the time base |
| TB.TF | total frequency power within the time base |
| P[] | |
| P.PSD[] | array of total power spectral density |
| P.valid | total valid time within period |
| P.LF | total low-frequency within period |
| P.MF | total mid-frequency within period |
| P.HF | total high-frequency within period |
| P.TF | total frequency power within period |

Figure 21:
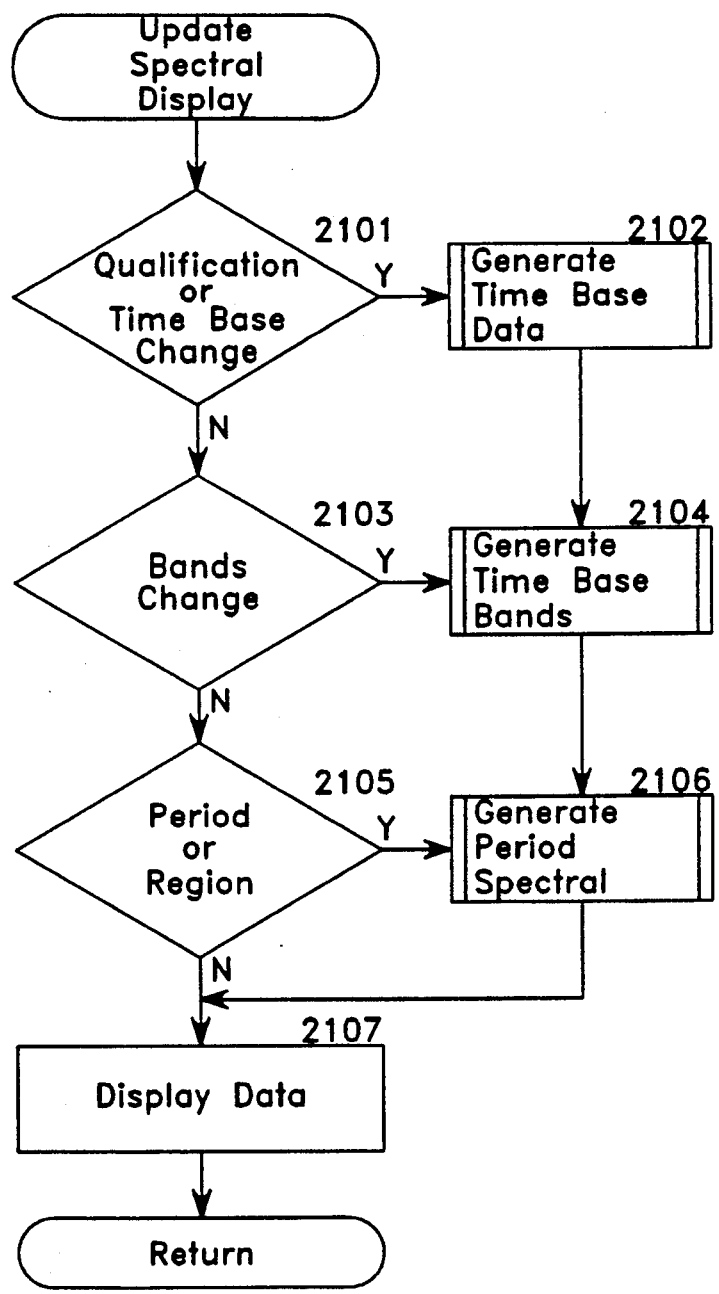
FIG. 21 is a flow diagram of the routine UpdateSpectralDisplay.

FIG. 21 is a flow diagram of the routine UpdateSpectralDisplay. This routine receives the beat data and user-specified qualifications and menu selections, generates the PSD data, and displays the data. In step 2101, if the interval qualifications or the time base has changed, then the routine continues at step 2102, else the routine continues at 2103. If the interval qualifications or time base changes, then the time base data needs to be regenerated. In step 2102, the routine invokes routine GenerateTimeBaseData to generate the time base data for each time base within the scan. In step 2103, if the frequency bands have changed, then the routine continues at step 2104, else the routine continues at 2105. If the frequency bands have changed, then the time base data is retotalled for the new frequency ranges. In step 2104, the routine invokes routine GenerateTimeBaseBands to accumulate the PSD data for the various frequency ranges for each time base within the scan. In step 2105, if the time period or region has changed, then the routine continues at 2106, else the routine continues at step 2107. If the time period or region changes, then the period data needs to be regenerated. In step 2107, the routine invokes routine GeneratePeriodSpectral to accumulate the period data. In step 2107, the routine displays the spectral data and returns.

Figure 22:
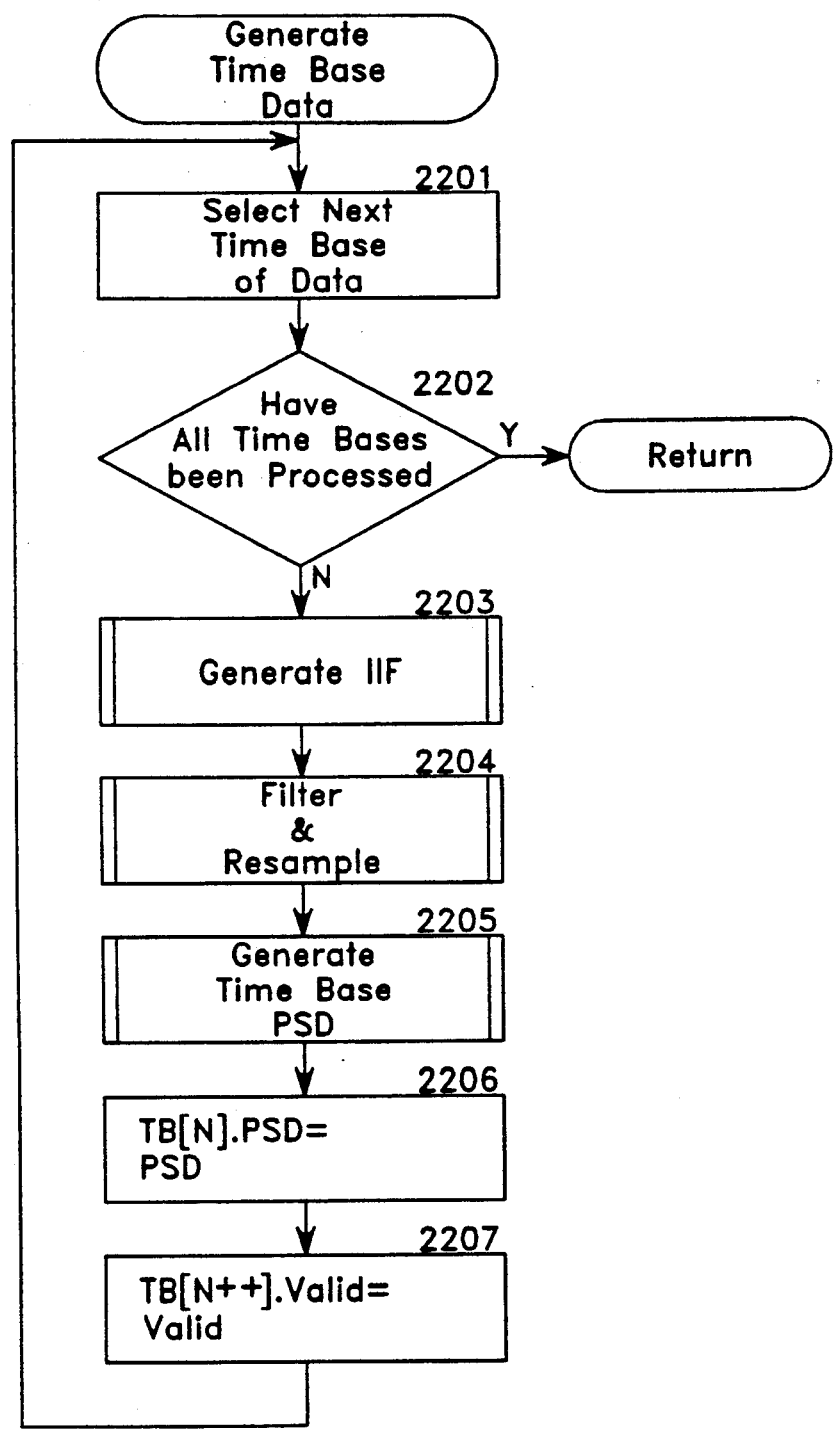
FIG. 22 is a flow diagram of routine GenerateTimeBaseData.

FIG. 22 is a flow diagram of routine GenerateTimeBaseData. This routine generates time base data for each time base within the scan. The time base data is accumulated in array TB. In step 2201, the routine selects the next time base of data in the scan, starting with the first. In step 2202, if all the time bases within the scan have been processed, then the routine returns, else the routine continues at step 2203. In step 2203, the routine invokes routine GenerateIIF to generate the instantaneous interval function (IIF) for the selected time base. In step 2204, the routine invokes routine Filter&Resample to filter the IIF data for the selected time base. In step 2205, the routine invokes routine GenerateTimeBasePSD to generate the PSD data. In steps 2206 and 2207, the routine stores the generated PSD data and valid times data in the time base array and increments index n into the array.

Figure 23A:
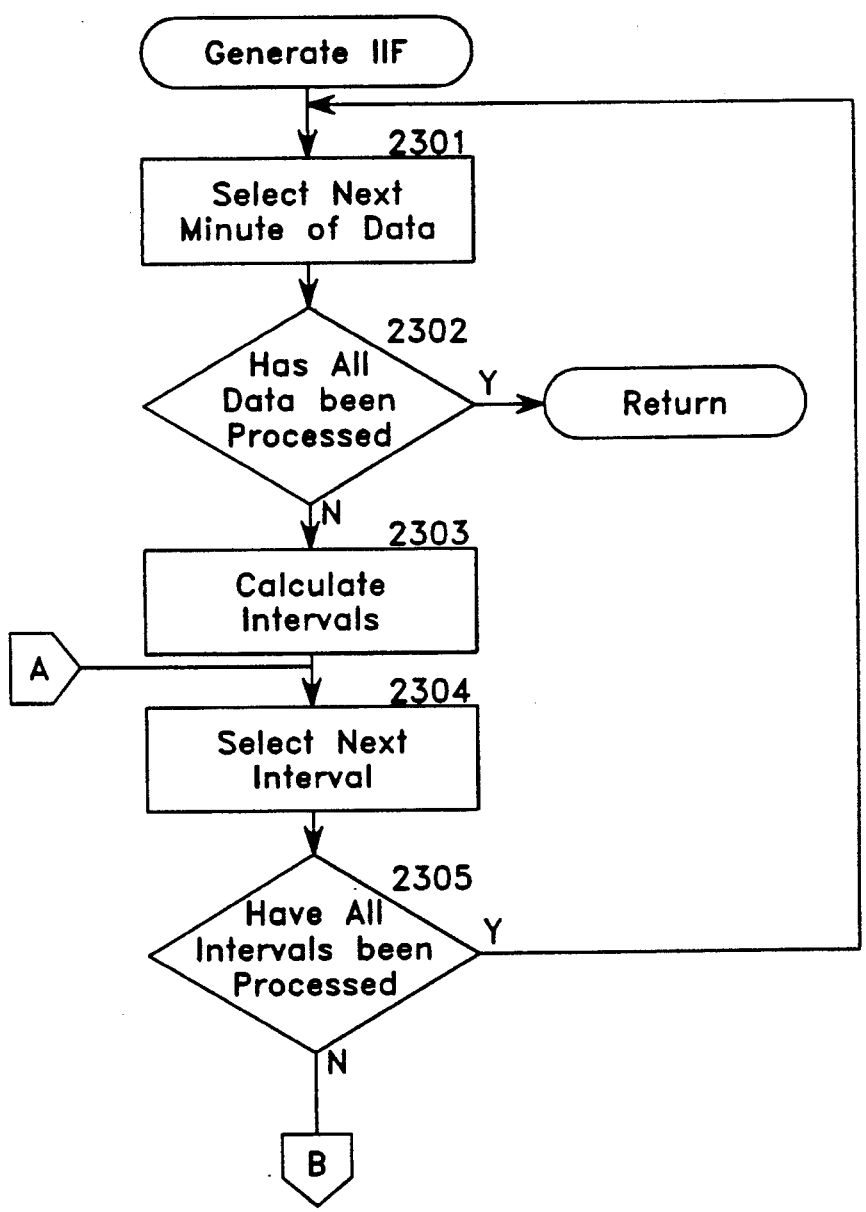
FIGS. 23A and 23B are flow diagrams of routine GenerateIIF.
Figure 23B:
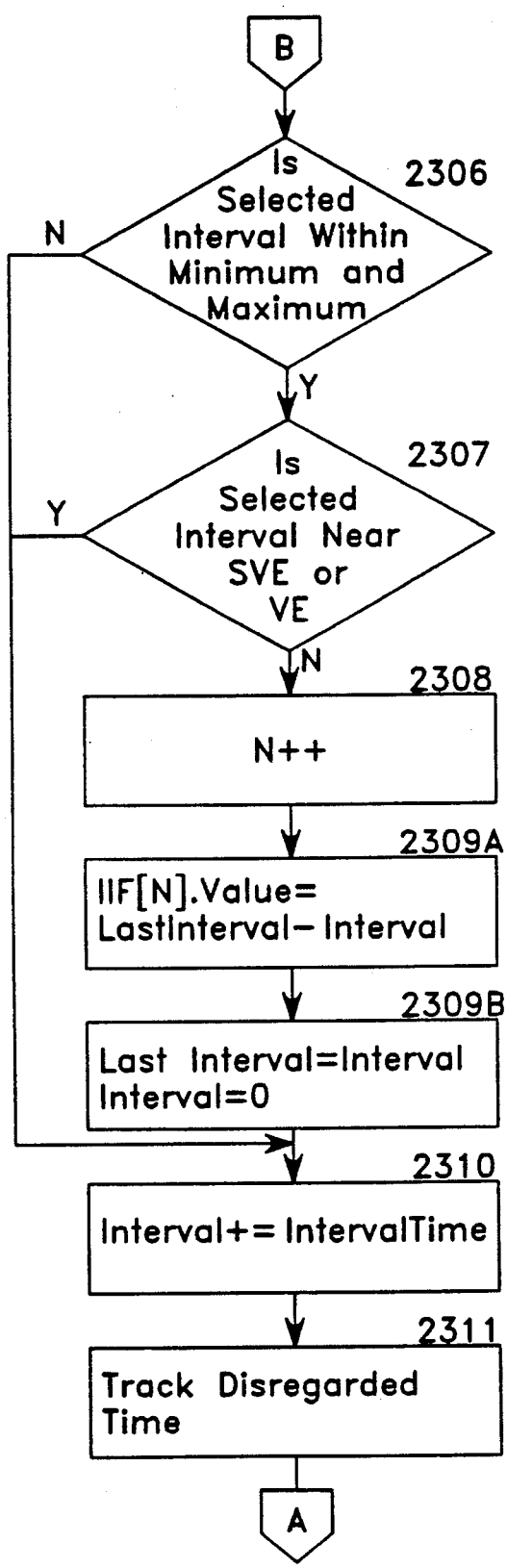

FIG. 23 is a flow diagram of routine GenerateIIF. This routine generates an instantaneous interval function for the selected time base. This routine corresponds to interval detector 2301 and IIF generator 2002. In step 2301, the routine selects the next minute of data within the selected time base, starting with the first minute. In step 2302, if all the data within the selected time base has been processed, then the routine returns, else the routine continues at step 2303. In step 2303, the routine generates the beat intervals in the selected minute of beat data. This process is described above in step 1103. In steps 2304 through 2311, the routine loops processing each interval within the selected minute and generating the instantaneous interval function. In step 2304, the routine selects the next interval within the selected minute of data. In step 2305, if all the intervals within the minute have been processed, then the routine loops to step 2301 to select the next minute of data, else the routine continues at 2306. In step 2306, if the selected interval is within the minimum and maximum interval qualification, then the routine continues at step 2307, else the routine continues at step 2310. In step 2307, if the selected interval is within the user-specified proximity of either an atrial or ventricular ectopic beat, then the interval is disregarded and the routine continues at step 2310, else the routine continues at step 2308. In step 2308, the routine increments index n, which serves as an index into array IIF. In step 2309A, the routine sets the value of the array IIF to the difference in time between the selected interval and the last interval, and sets the length of array IIF equal to the length of the current interval. In step 2309B, the routine updates the length of the last interval processed and initializes the length of current interval. In step 2310, the routine adds the time of the selected interval to the length of selected interval. The interval times of disregarded intervals are added to the length of the previous qualifying interval. In step 2311, the routine tracks the disregarded times f or use in determining whether a time base meets the user-specified time base qualification (percent of valid data) and the routine loops to step 2304.

Figure 24:
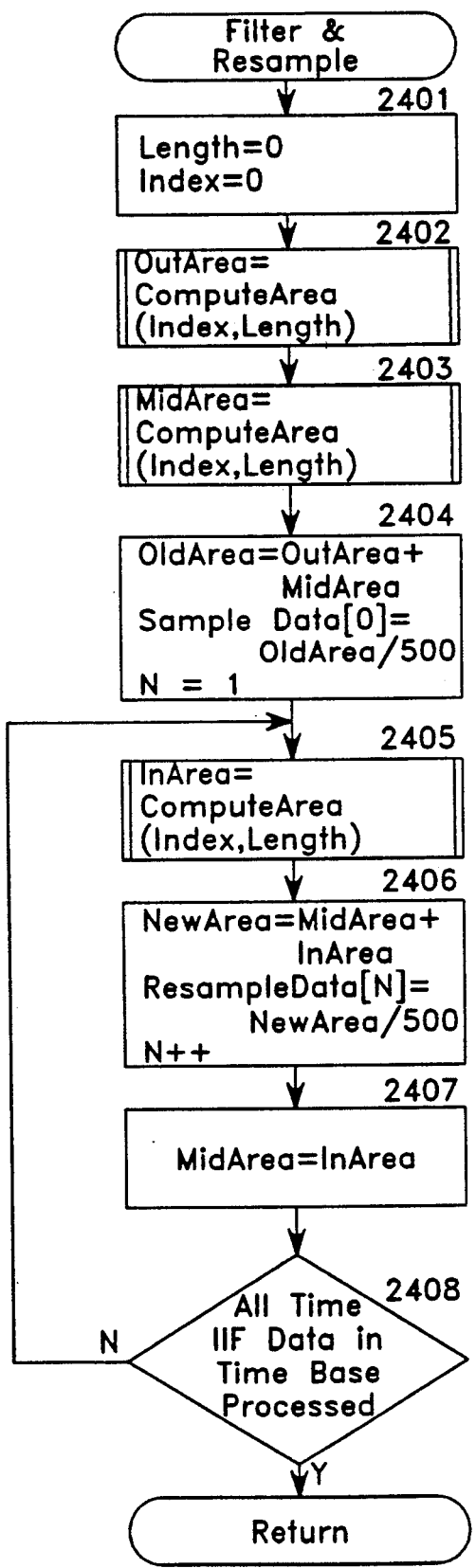
FIG. 24 is a flow diagram of routine Filter&Resample.

FIG. 24 is a flow diagram of routine Filter&Resample. This routine corresponds to the filter and Resampler 2003. In step 2401, the routine initializes variable Length and Index to 0. In step 2402, the routine invokes function ComputeArea and sets variable OutArea to the value returned. Function ComputeArea receives an index into the array IIF and a length parameter indicating the amount of time for the indicated index that has already been processed. The function calculates the area under the instantaneous interval function for a 500 millisecond period starting at the designated index and time of the IIF. The function updates the index and length, and returns the area as the value of the function. In step 2403, the routine sets variable MidArea equal to the value returned from invoking function ComputeArea. In step 2404, the routine sets variable oldarea equal to the sum of variable OutArea plus variable MidArea. The variable oldarea contains the area for the first 500 millisecond period of the scan period. The routine also sets the first entry in array ResampleData equal to variable OldArea divided by 500. The array ResampleData will contain the average area of the IIF per millisecond for each 250 millisecond period within the scan period. The routine also sets index n equal to 1. In steps 2405 through 2408, the routine loops calculating the area of the instantaneous interval function for each 250 millisecond interval and sets array ResampleData to the result. In step 2405, the routine sets variable InArea equal to the value returned from function ComputeArea. In step 2406, the routine sets variable NewArea equal to variable MidArea plus InArea. The variable NewArea contains the total area for a 500 millisecond time period. The routine sets the entry indexed by n in ResampleData equal to the variable NewArea divided by 500. The routine also increments index n to point to the next entry in array ResampleData. In step 2407, the routine sets variable MidArea equal to variable InArea. In step 2408, if all the IIF data for the selected time base has been processed, then the routine returns, else the routine loops to step 2405 to process the next 250 millisecond interval.

Figure 25:
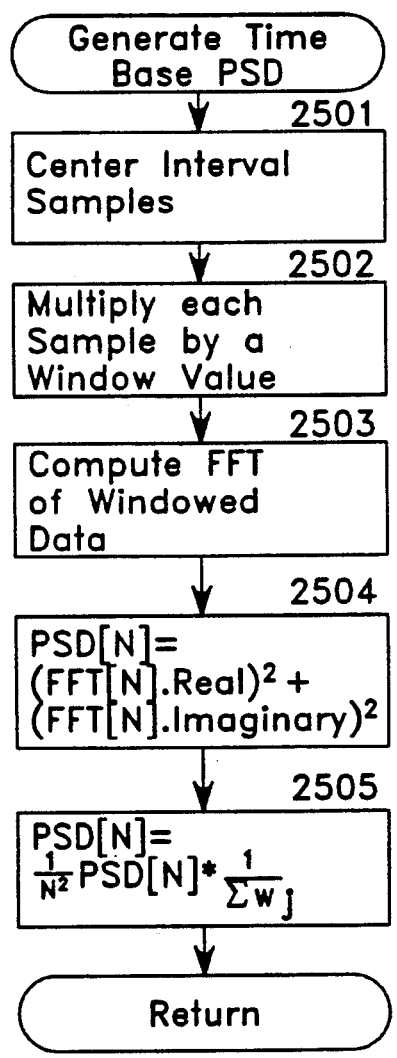
FIG. 25 is a flow diagram of routine GenerateTimeBasePSD.

FIG. 25 is a flow diagram of routine GenerateTimeBasePSD. This routine generates the PSD data f or the selected time base. This routine corresponds to PSD generator 2004. In step 2501, the routine centers the interval samples. The routine centers the interval samples to place the interval data in the center of the FFT window. For a 2-minute time base, there are 480 samples from the filter and resample function. Since the FFT is always performed with a power of 2, it is necessary to place the 480 samples in the middle of the 512 ($2^9$) sample window. Similarly, a 4-minute time base has 960 samples and the data is centered in the 1024 ($2^{10}$) FFT window. In step 2502, the routine multiplies each sample by a window value. In step 2503, the routine computes the FFT of the windowed data. In step 2504, the routine sets each entry in array PSD equal to the square of the real part plus the square of the imaginary part of the FFT. In step 2504, the routine divides each entry in array PSD by the product of the number of data points in the FFT squared times a window value. The routine then returns.

Figure 26:
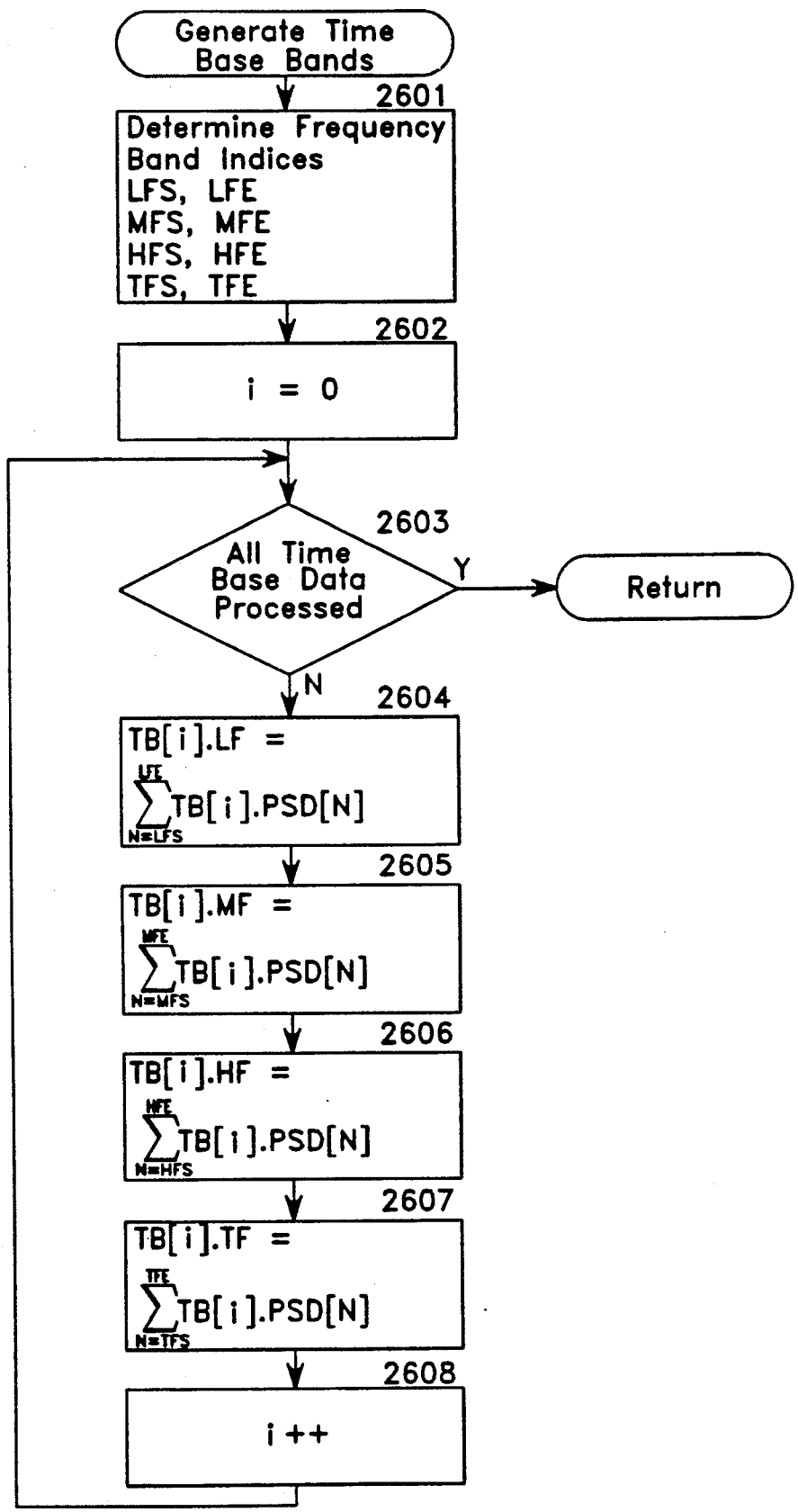
FIG. 26 is a flow diagram of routine GenerateTimeBaseBands.

FIG. 26 is a flow diagram of routine GenerateTimeBaseBands. This routine accumulates the total power spectral density for low frequency, mid frequency, high frequency, and total frequency for each time base. In step 2601, the routine determines the indices into the PSD arrays that correspond to the low frequency, mid frequency, high frequency, and total frequency start and end points. In step 2602, the routine initializes index i to 0. Index i is used as an index into array TB. In steps 2603 through 2608, the routine loops accumulating the totals for the various frequency ranges for each time base. In step 2603, if all the time base data has been processed, then the routine returns, else the routine continues at step 2604. In step 2604, the routine accumulates the total low-frequency power for the time base entry indexed by index i. In step 2605, the routine totals the total mid-frequency power for the time base indexed by index i. In step 2606, the routine totals the total high-frequency power for the time base indexed by index i. In step 2607, the routine totals the total frequency power for the time base indexed by index i. In step 2608, the routine increments index i and loops to step 2603 to process the next time base.

Figure 27:
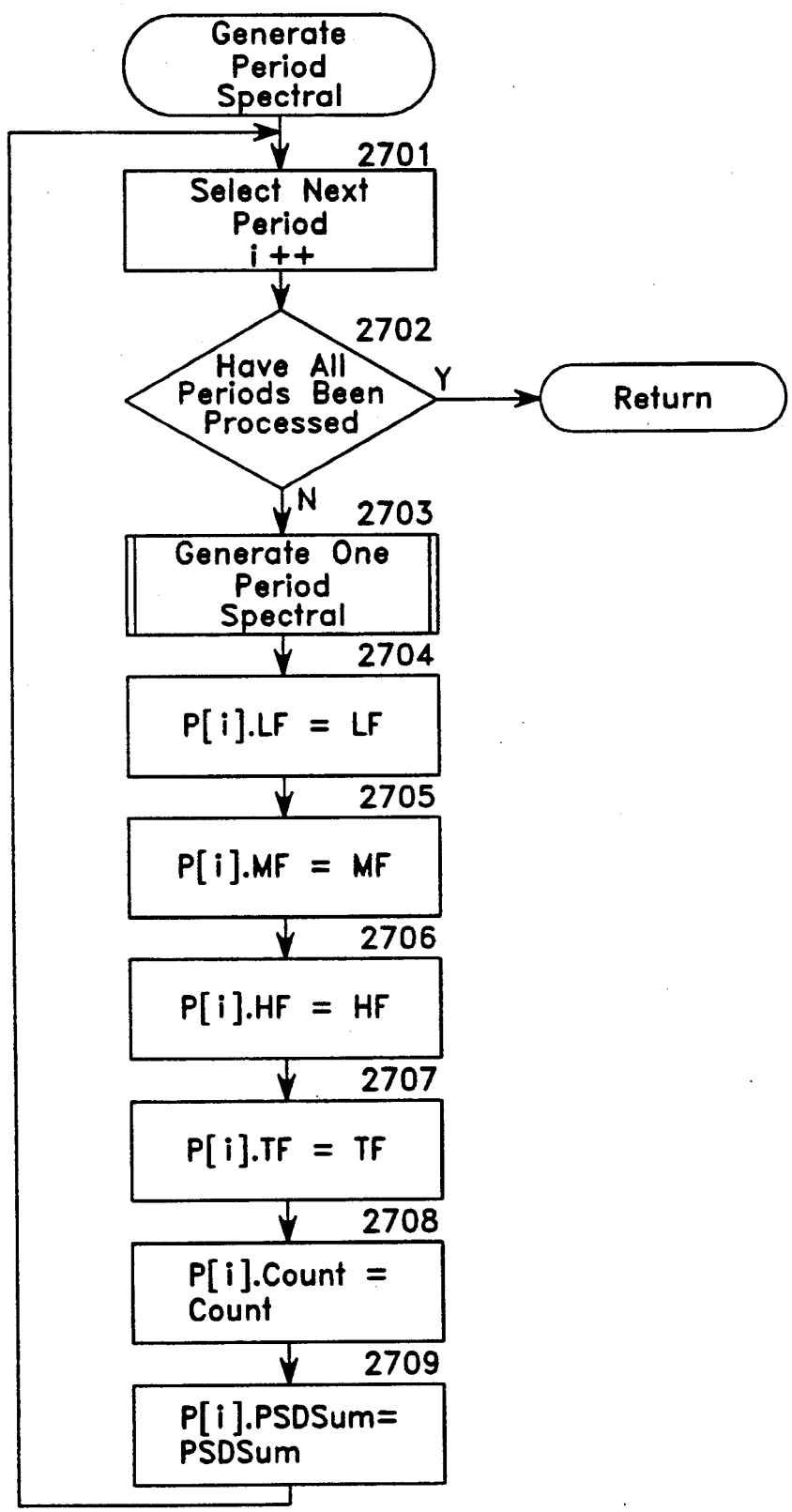
FIG. 27 is a flow diagram of the routine GeneratePeriodSpectral.

FIG. 27 is a flow diagram of the routine GeneratePeriodSpectral. This routine accumulates the spectral data for each period within the scan. This routine corresponds to the period spectral generator 2005. In step 2701, the routine selects the next period and increments index i. Index i is used as an index into array P which contains period spectral data. In step 2702, if all the periods have been processed, then the routine returns, else the routine continues at step 2703. In step 2703, the routine invokes routine GenerateOnePeriodSpectral, which accumulates the spectral data for the selected period. In steps 2704 through 2709, the routines sets the data in array P indexed by index i to the accumulated values and the routine loops to step 2701 to process the next period.

Figure 28A:
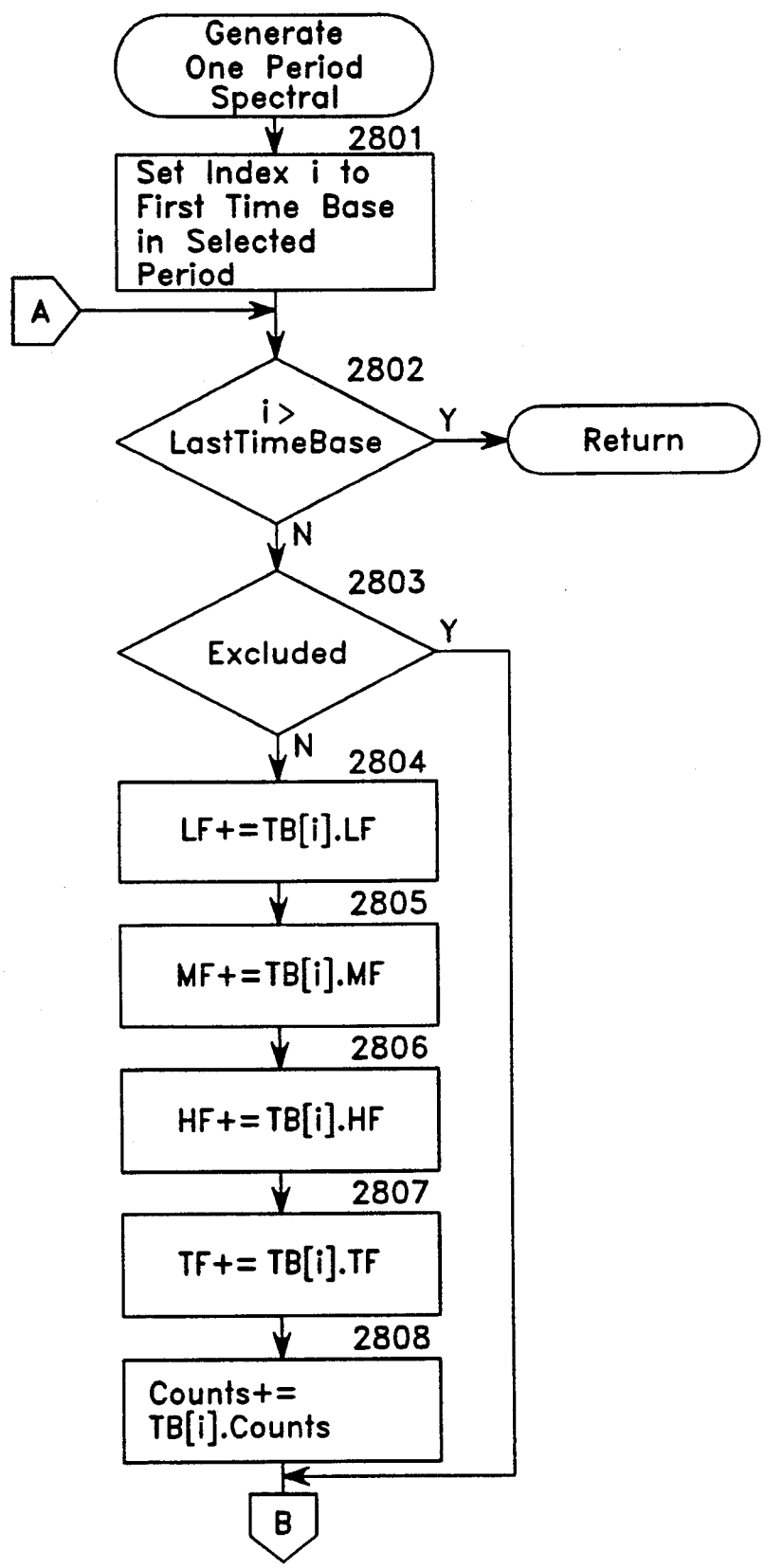
FIGS. 28A and 28B flow diagrams of routine GenerateOnePeriodSpectral.
Figure 28B:
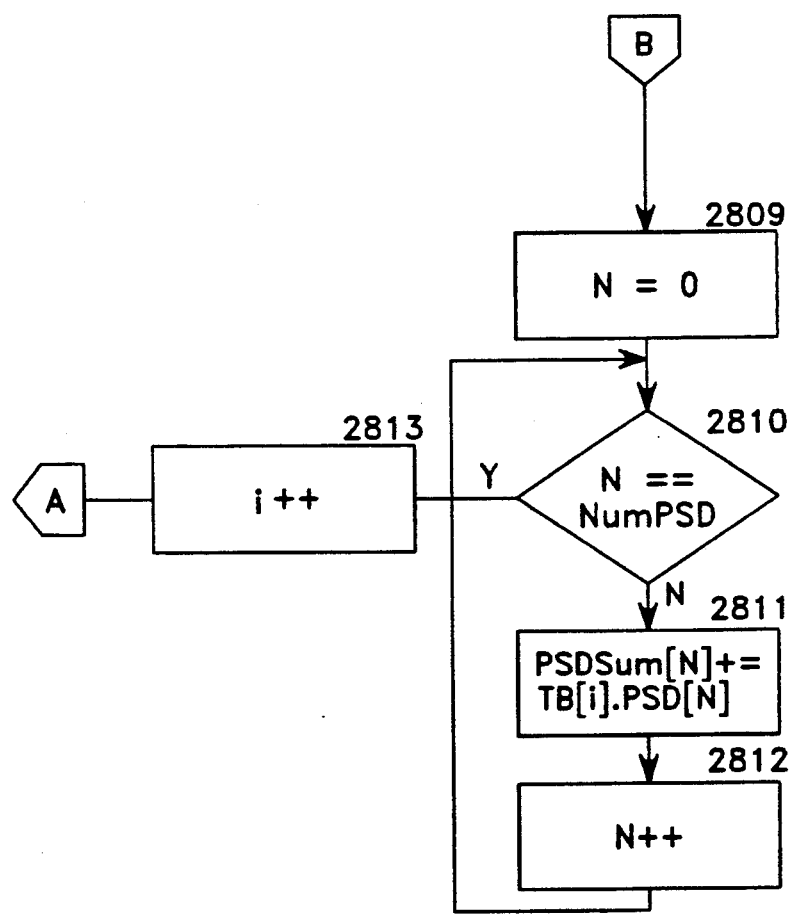

FIG. 28 is a flow diagram of routine GenerateOnePeriodSpectral. This routine accumulates the spectral data for each time base within the selected period. In step 2801, the routine sets index i to the first time base in the selected period. In steps 2802 through 2813, the routine loops accumulating the data for the selected time period. In step 2802, if index i is greater than the last time base within the selected time period, then the routine returns, else the routine continues at step 2803. In step 2803, if the time base indicated by index is excluded from the region, then the routine continues at step 2809, else the routine continues at step 2804. A time base is excluded either because its percent of valid data is less than the user-specified percentage or the time base is not with the user-specified region. In steps 2804 through 2808, the routine adds the total low-frequency, mid-frequency, high-frequency, and total frequency power for the time base indicated by index i into a running total for the selected period. In steps 2809 through 2812, the routine loops summing the power spectral density data for each point for the selected time base. In step 2813, the routine increments index i and loops to accumulate the next time base data.

Although the present invention has been described in terms of preferred embodiment, it is not intended that the invention be limited to these embodiments. Modifications within the spirit of the invention will be apparent to those skilled in the art. The scope of the present invention is defined by the claims that follow.

I claim:

1. A computer system for heart rate variability analysis of electrocardiographic data, the system comprising:
   a storage device having means for storing electrocardiographic data;
   an interval detector for determining the length of heart beat intervals in the electrocardiographic data;
   a minute data generator for accumulating statistical measurements based on the heart beat intervals and user-specified qualifications;
   a period data generator for accumulating statistical data measurements based on the generated minute data, a time period, and user-specified qualifications;
   a region data generator for accumulating statistical measurements based on the generated minute data and a region of time; and
   a display controller for displaying the period data and region data on a computer display device.

2. The computer system of claim 1 wherein the user-specified qualifications include a minimum and a maximum interval time, wherein intervals with interval times less than the minimum and greater than the maximum are not used to generate the minute data.

3. The computer system of claim 1 wherein the user-specified qualifications include a number of intervals before an atrial ectopic beat, wherein the number of intervals before an atrial ectopic beat are not used to generate the minute data.

4. The computer system of claim 1 wherein the user-specified qualifications include a number of intervals after an atrial ectopic beat, wherein the number of intervals after an atrial ectopic beat are not used to generate the minute data.

5. The computer system of claim 1 wherein the user-specified qualifications include a number of intervals before a ventricular ectopic beat, wherein the number of intervals before a ventricular ectopic beat are not used to generate the minute data.

6. The computer system of claim 1 wherein the user-specified qualifications include a number of intervals after a ventricular ectopic beat, wherein the number of intervals after a ventricular ectopic beat are not used to generate the minute data.

7. The computer system of claim 1 wherein the user-specified qualifications include a minimum number of intervals per minute, wherein when the period data generator determines that a minute of electrocardiographic data has less than the minimum number of intervals, then minute data from that minute is not used to generate interval period data.

8. The computer system of claim 1 wherein the user-specified qualifications include a minimum number of triplets per minute, wherein when the period data generator determines that a minute of electrocardiographic data has less than the minimum number of triplets, then minute data from that minute is not used to generate difference period data.

9. The computer system of claim 1 wherein the user-specified qualifications include a difference margin for the difference in time of intervals that comprise a triplet, wherein when the difference exceeds the difference margin, the triplet will be used to compute %RRxx.

10. The computer system of claim 1 wherein the period data is displayed in tabular format on the computer display device in response to a user selection of tabular format and the period data is displayed in graphic format on the computer display device in response to the user selection of graphical format.

11. The computer system of claim 1 wherein the user-specified qualifications include the number of minutes of minute data to be accumulated into one time period of period data.

12. The computer system of claim 1 wherein the display controller includes means for simultaneously displaying on the computer display device generated region data and generated period data.

13. The computer system of claim 12 including:
   means for receiving a user-specified region of time; and
   means for updating displayed region data in response to receiving a user-specified region of time.

14. The computer system of claim 1 wherein when period data corresponds to a period within a user-specified region of time, then the period data is displayed with an indicator that the period is within the user-specified region.

15. The computer system of claim 14 wherein when period data corresponds to periods not within the user-specified region of time, then the period data is displayed with an indicator that the period is not within the user-specified region.

16. The computer system of claim 1 wherein period data that corresponds to periods not within a user-specified region of time is not displayed.

17. A computer system for heart rate variability analysis of electrocardiographic data, the system comprising:
a storage device having means for storing electrocardiographic data;
an interval detector for determining the length of heart beat intervals in electrocardiographic data;
an instantaneous interval function generator for generating instantaneous interval function data based on the interval data and user-specified qualifications;
a filter and resampler for generating resampled data by filtering and resampling the instantaneous interval function data;
a power spectral density data generator for generating spectral density data based on the resampled data, a time base specifying the period over which the data is generated, and user-specified qualifications;
a period spectral data generator for accumulating period spectral data measurements and region spectral data measurements based on the generated power spectral density, a time period, and user-specified qualifications; and
a display controller for displaying the period data and region data on a computer display device.

18. The computer system of claim 17 wherein the user-specified qualifications include a minimum and a maximum interval time, wherein a first interval with an interval time that is between the minimum and maximum interval times has its interval time increased by the interval time of a second interval when the interval time of the second interval is less than the minimum or greater than the maximum interval time.

19. The computer system of claim 17 wherein the user-specified qualifications include a number of intervals before an atrial ectopic beat, wherein the number of intervals before an atrial ectopic beat are not used to generate the instantaneous interval function data.

20. The computer system of claim 17 wherein the user-specified qualifications include a number of intervals after an atrial ectopic beat, wherein the number of intervals after an atrial ectopic beat are not used to generate the instantaneous interval function data.

21. The computer system of claim 17 wherein the user-specified qualifications include a number of intervals before a ventricular ectopic beat, wherein the number of intervals before a ventricular ectopic beat are not used to generate the instantaneous interval function data.

22. The computer system of claim 17 wherein the user-specified qualifications include a number of intervals after a ventricular ectopic beat, wherein the number of intervals after a ventricular ectopic beat are not used to generate the instantaneous interval function data.

23. The computer system of claim 17 wherein the time base is a user-specified time base.

24. The computer system of claim 17 wherein the user-specified qualifications include a percent of valid data, and wherein when a time base of data has less than the percent of valid data, then the period spectral data generator excludes the power spectral density data for that time base from the accumulation of power spectral density data for the period.

25. The computer system of claim 17 wherein the user-specified qualifications include frequency ranges, wherein the computer system accumulates total power within each frequency range.

26. The computer system of claim 17 wherein the display controller displays a graph of the period data on the computer display device.

27. The computer system of claim 17 wherein when period data corresponds to a period within a user-specified region, then the period data is displayed with an indicator that the period is within the user-specified region.

28. The computer system of claim 17 wherein the user-specified qualifications indicate that the period data is to include an accumulation of the power spectral density data for all of the electrocardiographic data.

29. The computer system of claim 17 wherein graphs of the power spectral density data for successive time periods are automatically displayed at a user-specified rate.

30. The computer system of claim 17 wherein the display controller displays total power spectral density data for a user-specified frequency range in graphical format.

31. The computer system of claim 17 wherein the display controller displays the ratio of the total power of two frequency ranges in graphical format.

32. The computer system of claim 17 wherein the display controller including means for simultaneously displaying on the computer display device generated region data and generated period data.

33. The computer system of claim 32 including:
means for receiving a user-specified region of time; and
means for updating displayed region data in response to receiving a user-specified region of time.

* * * * *